US010988510B2

(12) United States Patent
Lindner et al.

(10) Patent No.: US 10,988,510 B2
(45) Date of Patent: *Apr. 27, 2021

(54) SECRETAGOGUES DERIVED FROM OXALOBACTER FORMIGENES

(71) Applicant: OXTHERA INTELLECTUAL PROPERTY AB, Stockholm (SE)

(72) Inventors: Elisabeth Lindner, Stockholm (SE); Helena Cowley, Gainesville, FL (US); Aaron Cowley, Gainesville, FL (US); Maria Åkerman, Sollentuna (SE)

(73) Assignee: OXTHERA INTELLECTUAL PROPERTY AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/145,063

(22) Filed: Sep. 27, 2018

(65) Prior Publication Data

US 2019/0085035 A1 Mar. 21, 2019

Related U.S. Application Data

(63) Continuation of application No. 14/902,484, filed as application No. PCT/SE2014/050848 on Jul. 3, 2014, now Pat. No. 10,125,176.

(30) Foreign Application Priority Data

Jul. 5, 2013 (WO) ............... PCT/SE2013/050875

(51) Int. Cl.
| *C07K 14/195* | (2006.01) |
| *A61K 38/16* | (2006.01) |
| *C12N 9/04* | (2006.01) |
| *C12N 9/06* | (2006.01) |
| *C12N 9/02* | (2006.01) |
| *C12N 9/10* | (2006.01) |
| *C12N 9/14* | (2006.01) |
| *C12N 9/88* | (2006.01) |
| *A61K 35/74* | (2015.01) |
| *A61K 38/00* | (2006.01) |

(52) U.S. Cl.
CPC .......... *C07K 14/195* (2013.01); *A61K 38/164* (2013.01); *C12N 9/0006* (2013.01); *C12N 9/0016* (2013.01); *C12N 9/0051* (2013.01); *C12N 9/1014* (2013.01); *C12N 9/1085* (2013.01); *C12N 9/14* (2013.01); *C12N 9/88* (2013.01); *A61K 35/74* (2013.01); *A61K 38/00* (2013.01); *C12Y 101/0106* (2013.01); *C12Y 104/01016* (2013.01); *C12Y 108/01* (2013.01); *C12Y 201/02001* (2013.01); *C12Y 205/01006* (2013.01); *C12Y 205/01009* (2013.01); *C12Y 205/01047* (2013.01); *C12Y 303/01001* (2013.01); *C12Y 402/01003* (2013.01)

(58) Field of Classification Search
CPC ...... A61K 35/74; A61K 38/00; A61K 38/164; A61K 35/741; C07K 14/195; C07K 14/00; C12N 9/0006; C12N 9/0016; C12N 9/0051; C12N 9/1014; C12N 9/1085; C12N 9/14; C12N 9/88; C12Y 101/0106; C12Y 108/01; C12Y 201/02001; C12Y 205/01006; C12Y 205/01009; C12Y 205/01047; C12Y 303/01001; C12Y 402/01003; C12Y 104/01016; A61P 13/00; A61P 13/04; A61P 19/06; A61P 1/00; A61P 1/04; A61P 3/00; A61P 3/10; A61P 9/00

See application file for complete search history.

(56) References Cited

U.S. PATENT DOCUMENTS

| 10,125,176 B2 | 11/2018 | Lindner et al. |
| 2004/0234514 A1 | 11/2004 | Sidhu et al. |
| 2005/0232901 A1 | 10/2005 | Zaghmout |
| 2007/0178070 A1 | 8/2007 | Kaul et al. |
| 2008/0038246 A1 | 2/2008 | Shenoy et al. |

FOREIGN PATENT DOCUMENTS

| WO | WO 2005/097176 A2 | 10/2005 |
| WO | WO-2009/134339 A2 | 11/2009 |

OTHER PUBLICATIONS

Knight et al "The genetic composition of Oxalobacter formigenes and its rel. to col. and calcium oxalate stone disease", Urolithiasis. Jun. 2013: 41(3): 187-196. 2013.*
Hoppe et al., "Efficacy and safety of Oxalobacter formigenes to reduce urinary oxalate in primary hyperoxaluria," Nephrology Dialysis Transplantation, vol. 26, No. 11, pp. 3609-3615, Nov. 2011.
International Search Report dated Oct. 14, 2014 in application No. PCT/SE2014/050848.
Hassan et al., "Cholinergic signaling inhibits oxalate transport by human intestinal T84 cells," Am. J. Physiol. Cell Physiol., vol. 302, pp. C46-C58, 2012 (first published Sep. 28, 2011).
Aronson, "Role of SLC26A6-mediated Cl-oxalate exchange in renal physiology and pathophysiology," J. Nephrol., vol. 23, Suppl. 16, pp. S158-S164, Nov.-Dec. 2010 (Abstract).
Office Action dated Jul. 17, 2018 in CN application 201480038544. 5.

(Continued)

*Primary Examiner* — Deborah K Ware
(74) *Attorney, Agent, or Firm* — Foley & Lardner LLP

(57) ABSTRACT

The present invention relates to a secretagogue compound derived from oxalate degrading bacteria, for use in the treatment of an oxalate related disease and/or oxalate related imbalance in a subject, wherein the administration of the secretagogue results in a reduction of urinary oxalate and/or plasma oxalate in the subject. The invention further relates to a pharmaceutical composition comprising such a secretagogue compound, a method for treating a subject suffering from an oxalate related disease, and to a method for preparing a secretagogue.

17 Claims, 3 Drawing Sheets

Specification includes a Sequence Listing.

(56) References Cited

OTHER PUBLICATIONS

Turroni et al., "Oxalate-Degrading Activity in *Bifidobacterium animalis* subsp. *lactis*: Impact of Acidic Conditions on the Transcriptional Levels of the Oxalyl Coenzyme A (CoA) Decarboxylase and Formyl-CoA Transferase Genes," Applied and Environmental Microbioloby, vol. 76, No. 16, pp. 5609-5620 (Aug. 2010).

* cited by examiner

SEQUENCE LISTING

<160> NUMBER OF SEQ ID NOS: 19

<210> SEQ ID NO 1
<211> LENGTH: 295
<212> TYPE: PRT
<213> ORGANISM: Oxalobacter formigenes

```
<400> SEQUENCE: 1

Met Ala Asn Leu Gly Phe Ile Gly Leu Gly Ile Met Gly Val Pro Met
1               5                   10                  15

Ala Val Asn Leu Gln Asn Gly Gly Asn Lys Leu Phe Val Asn Asp Lys
                20                  25                  30

Lys Ala Pro Pro Ala Ala Leu Thr Asp Gly Ala Lys Ala Cys Ala
            35                  40                  45

Thr Gly Ala Glu Val Ala Lys Asn Ala Asp Ile Phe Ile Met Val
    50                  55                  60

Pro Asp Thr Pro Asp Val Glu Ala Val Leu Phe Gly Glu Asn Gly Val
65              70                  75                  80

Ala Gln Gly Leu Ser Ala Gly Lys Ile Val Val Asp Met Ser Ser Ile
                85                  90                  95

Ser Pro Ile Ala Thr Lys Glu Phe Ala Lys Lys Ile Asn Asp Leu Gly
            100                 105                 110

Cys Glu Tyr Leu Asp Ala Pro Val Ser Gly Gly Glu Val Gly Ala Lys
            115                 120                 125

Ala Gly Ser Leu Thr Ile Met Val Gly Gly Lys Glu Glu Thr Phe Asn
            130                 135                 140

Lys Val Lys Pro Leu Phe Glu Leu Met Gly Lys Asn Ile Thr Leu Val
145                 150                 155                 160

Gly Gly Asn Gly Asp Gly Gln Thr Thr Lys Val Ala Asn Gln Ile Ile
                165                 170                 175

Val Ala Leu Asn Ile Gln Ala Val Ala Glu Ala Leu Leu Phe Ala Ser
            180                 185                 190

Lys Ala Gly Ala Asp Pro Ala Lys Val Arg Gln Ala Leu Met Gly Gly
            195                 200                 205

Phe Ala Ser Ser Arg Ile Leu Glu Val His Gly Glu Arg Met Ile Asn
210                 215                 220

Arg Thr Phe Asn Pro Gly Phe Arg Ile Asn Leu His Gln Lys Asp Leu
225                 230                 235                 240

Asn Leu Ala Leu Gln Gly Ala Lys Ala Leu Gly Ile Ser Leu Pro Asn
            245                 250                 255

Thr Ala Thr Ala Gln Glu Leu Met Asn Ala Cys Ala Ala Asn Gly Leu
            260                 265                 270

Ser Gly Met Asp His Ser Ala Leu Cys Arg Ala Val Glu Ile Met Ser
            275                 280                 285

Ala His Glu Ile Ala Lys Ala
            290                 295

<210> SEQ ID NO 2
<211> LENGTH: 310
<212> TYPE: PRT
<213> ORGANISM: Oxalobacter formigenes

<400> SEQUENCE: 2

Met Ser Asn Ile Ala Lys Ser Ala Thr Asp Leu Ile Gly Asn Thr Pro
1               5                   10                  15

Leu Leu Glu Ile Ser Arg Phe Gly Lys His Val Asp Ala Asp Ala Thr
                20                  25                  30

Ile Leu Ala Lys Leu Glu Tyr Phe Asn Pro Ala Gly Ser Ala Lys Asp
            35                  40                  45

Arg Ile Ala Lys Ala Met Ile Asp Ala Ala Glu Ala Asp Gly Lys Leu
            50                  55                  60
```

Ile Pro Gly Ser Thr Ile Glu Pro Thr Ser Gly Asn Thr Gly Ile
65                  70                  75                  80

Ala Leu Ala Ala Val Gly Ala Ala Arg Gly Tyr Arg Val Ile Ile Thr
                85                  90                  95

Met Pro Glu Thr Met Ser Val Glu Arg Gln Lys Leu Ile Arg Gly Tyr
            100                 105                 110

Gly Ala Asp Leu Val Leu Thr Glu Gly Ala Lys Gly Met Lys Gly Ala
            115                 120                 125

Ile Glu Lys Ala Gln Glu Leu Ala Ala Thr Ile Pro Gly Gly Phe Val
            130                 135                 140

Pro Leu Gln Phe Ala Asn Pro Ala Asn Pro Ala Ile His Lys Ala Thr
145                 150                 155                 160

Thr Gly Pro Glu Ile Trp Arg Asp Thr Asp Gly Lys Val Asp Ile Phe
            165                 170                 175

Val Ala Gly Val Gly Thr Gly Gly Thr Leu Thr Gly Val Gly Lys Tyr
            180                 185                 190

Leu Lys Glu Gln Asn Pro Ala Val Gln Val Val Ala Ile Glu Pro Ala
            195                 200                 205

Ala Ser Pro Val Leu Ala Gly Gly Lys Pro Gly Pro His Lys Ile Gln
            210                 215                 220

Gly Ile Gly Ala Gly Phe Ile Pro Glu Ala Leu Asp Val Asn Val Phe
225                 230                 235                 240

Asp Glu Val Ile Gly Val Pro Asn Asp Ala Ala Phe Ala Thr Ala Lys
                245                 250                 255

Thr Leu Ala His Ala Glu Gly Val Leu Val Gly Ile Ser Ser Gly Ala
            260                 265                 270

Ala Leu Trp Ala Ala Ser Glu Leu Ala Lys Arg Pro Glu Asn Arg Gly
            275                 280                 285

Lys Thr Ile Val Val Leu Leu Ala Asp Asn Gly Glu Arg Tyr Leu Ser
            290                 295                 300

Thr Asp Leu Phe Ser Asn
305                 310

<210> SEQ ID NO 3
<211> LENGTH: 79
<212> TYPE: PRT
<213> ORGANISM: Oxalobacter formigenes

<400> SEQUENCE: 3

Met Ser Asp Ile Glu Gln Arg Val Lys Lys Ile Val Ala Glu Gln Leu
1               5                   10                  15

Gly Val Ala Glu Asp Glu Ile Lys Leu Glu Ser Ser Phe Val Asp Asp
            20                  25                  30

Leu Gly Ala Asp Ser Leu Asp Thr Val Glu Leu Val Met Ala Leu Glu
            35                  40                  45

Asp Glu Phe Glu Ile Glu Ile Pro Asp Glu Gln Ala Glu Lys Ile Thr
            50                  55                  60

Thr Val Gln Gln Ala Val Asp Tyr Ala Thr Ala Asn Met Gln Ser
65                  70                  75

<210> SEQ ID NO 4
<211> LENGTH: 96
<212> TYPE: PRT
<213> ORGANISM: Oxalobacter formigenes

<400> SEQUENCE: 4

Met Lys Leu Arg Pro Leu Gln Asp Arg Ile Val Lys Arg Val Asp
1               5                   10                  15

Gln Glu Lys Thr Thr Ala Ser Gly Ile Val Ile Pro Asn Ala Ala
            20                  25                  30

Glu Lys Pro Asp Gln Gly Glu Val Ile Ala Val Gly Asn Gly Lys Val
        35                  40                  45

Leu Glu Asp Gly Lys Val Leu Pro Leu Asp Val Lys Val Gly Asp Ile
50                  55                  60

Val Leu Phe Gly Lys Tyr Ser Gly Gln Thr Val Lys Val Glu Gly Glu
65                  70                  75                  80

Glu Leu Leu Val Met His Glu Ser Asp Val Met Ala Ile Val Gln Asn
                85                  90                  95

<210> SEQ ID NO 5
<211> LENGTH: 387
<212> TYPE: PRT
<213> ORGANISM: Oxalobacter formigenes

<400> SEQUENCE: 5

Met Ser Gln Asp Tyr Leu Phe Thr Ser Glu Ser Val Ser Glu Gly His
1               5                   10                  15

Pro Asp Lys Val Ala Asp Gln Ile Ser Asp Ala Ile Leu Asp Ala Ile
            20                  25                  30

Leu Glu Gln Asp Pro His Ala Arg Val Ala Ala Glu Thr Leu Cys Asn
        35                  40                  45

Thr Gly Leu Val Val Leu Ala Gly Glu Ile Thr Thr Thr Ala Asn Ile
50                  55                  60

Asp Tyr Ile Ser Val Ala Arg Asp Thr Ile Lys Arg Ile Gly Tyr Asp
65                  70                  75                  80

Asn Asn Asp Tyr Gly Ile Asp His Arg Gly Cys Ala Val Leu Val Gly
                85                  90                  95

Tyr Asp Lys Gln Ser Pro Asp Ile Ala Gln Gly Val Asp Glu Gly Arg
            100                 105                 110

Gly Ile Asp Leu Asp Gln Gly Ala Gly Asp Gln Gly Leu Met Phe Gly
        115                 120                 125

Tyr Ala Cys Asp Glu Thr Pro Glu Leu Met Pro Ala Ala Ile Tyr Tyr
130                 135                 140

Ala His Arg Leu Val Glu Arg Gln Ser Gln Leu Arg Lys Asp Gly Arg
145                 150                 155                 160

Ile Ala Trp Leu Arg Pro Asp Ala Lys Ser Gln Val Thr Leu Arg Tyr
                165                 170                 175

Val Asp Gly Lys Pro Val Ala Ala Glu Thr Ile Val Leu Ser Thr Gln
            180                 185                 190

His Ala Pro Glu Val Glu His Lys Gln Ile Glu Glu Ala Val Ile Glu
        195                 200                 205

Glu Ile Ile Lys Pro Val Met Pro Ala Glu Trp Leu Lys Glu Ser Lys
210                 215                 220

Tyr Leu Val Asn Pro Thr Gly Arg Phe Val Ile Gly Gly Pro Gln Gly
225                 230                 235                 240

Asp Cys Gly Leu Thr Gly Arg Lys Ile Ile Val Asp Thr Tyr Gly Gly
                245                 250                 255

Ser Cys Pro His Gly Gly Gly Ala Phe Ser Gly Lys Asp Pro Ser Lys
            260                 265                 270

Val Asp Arg Ser Ala Ala Tyr Ala Ala Arg Tyr Val Ala Lys Asn Ile
        275                 280                 285

Val Ala Ala Gly Leu Ala Lys Lys Cys Gln Ile Gln Val Ser Tyr Ala
    290                 295                 300

Ile Gly Val Ala Arg Pro Ile Asn Ile Thr Ile Asn Thr Glu Gly Thr
305                 310                 315                 320

Gly Val Ile Ala Asp Ser Lys Ile Ala Ala Leu Val Asn Asp His Phe
                325                 330                 335

Asp Leu Arg Pro Lys Gly Ile Val Gln Met Leu Asp Leu Leu His Pro
                340                 345                 350

Arg Tyr Val Lys Thr Ala Ala Tyr Gly His Phe Gly Arg Asp Glu Pro
            355                 360                 365

Glu Phe Thr Trp Glu Lys Thr Asp Lys Ala Ala Asp Leu Arg Gln Ala
    370                 375                 380

Ala Gly Leu
385

<210> SEQ ID NO 6
<211> LENGTH: 126
<212> TYPE: PRT
<213> ORGANISM: Oxalobacter formigenes

<400> SEQUENCE: 6

Met Met Ser Lys Lys Leu Leu Thr Gly Leu Phe Ala Ala Gly Leu Ser
1               5                   10                  15

Ile Gly Met Leu Ala Val Ser Ser Thr Ala Ser Ala Gln Tyr Ile Gly
                20                  25                  30

Pro Thr Arg Ile Ala Pro Thr Thr Val Asn Lys Val Leu Lys Ser Pro
            35                  40                  45

Val Asp Asp Gln Tyr Val Leu Leu Ser Gly Lys Ile Thr Ser Gln Val
        50                  55                  60

Ser Lys Asp Lys Tyr Thr Phe Thr Asp Lys Thr Gly Ser Ile Val Val
65                  70                  75                  80

Glu Ile Asp Asn Glu Val Phe Ala Gly Arg Gln Val Gly Pro Asp Thr
                85                  90                  95

Gln Val Glu Ile Trp Gly Lys Val Asp Lys Asp Met Phe Lys Glu Pro
            100                 105                 110

Lys Ile Asp Val Lys Arg Leu Gly Ile Pro Asn Gln Thr Lys
        115                 120                 125

<210> SEQ ID NO 7
<211> LENGTH: 162
<212> TYPE: PRT
<213> ORGANISM: Oxalobacter formigenes

<400> SEQUENCE: 7

Met Met Thr Val Asn Thr Phe Glu Ile Asp Leu Gln Gly Gln Asp Leu
1               5                   10                  15

Arg Ile Gly Ile Val Gln Ser Arg Phe Asn Glu Glu Ile Cys Arg Gly
                20                  25                  30

Leu Leu Gly Ala Cys Leu Glu Glu Leu Lys Arg Leu Gly Val Ala Asp
            35                  40                  45

Glu Asp Ile Leu Val Ala Thr Val Pro Gly Ala Leu Glu Ile Pro Thr
        50                  55                  60

Ala Leu Gln Lys Met Ala Glu Ser Gln Gln Phe Asp Ala Leu Ile Ala
65                  70                  75                  80

Val Gly Gly Ile Ile Lys Gly Glu Thr Tyr His Phe Glu Leu Val Ser
                85                  90                  95

```
Asn Glu Ser Ala Ala Gly Ile Ser Arg Val Ala Leu Asp Phe Asp Met
            100                 105                 110

Pro Ile Ala Asn Ala Ile Leu Thr Thr Tyr Thr Asp Glu Gln Ala Glu
            115                 120                 125

Ala Arg Met Val Glu Lys Gly Thr Glu Ala Ala Arg Val Ala Val Glu
130                 135                 140

Met Ala Asn Leu Val Met Ala Ile Asp Glu Leu Glu Pro Pro Glu Glu
145                 150                 155                 160

Asp Glu

<210> SEQ ID NO 8
<211> LENGTH: 188
<212> TYPE: PRT
<213> ORGANISM: Oxalobacter formigenes

<400> SEQUENCE: 8

Met Ser Ser Leu Ile Asn Thr Glu Ile Ile Pro Phe Lys Ala Gln Ala
1               5                   10                  15

Tyr His Asn Gly Gln Phe Val Lys Val Thr Asp Ala Asp Leu Lys Gly
            20                  25                  30

Lys Trp Ser Val Val Phe Phe Tyr Pro Ala Asp Phe Ser Phe Val Cys
        35                  40                  45

Pro Thr Glu Leu Gly Asp Leu Ala Asp His Tyr Glu Glu Phe Lys Lys
    50                  55                  60

Leu Gly Val Glu Ile Tyr Ser Val Ser Thr Asp Thr His Phe Val His
65                  70                  75                  80

Lys Gly Trp His Asp Ala Ser Asp Thr Ile Lys Lys Ile Gln Phe Pro
                85                  90                  95

Met Val Gly Asp Pro Ser Gly Gln Ile Ser Arg Asn Phe Asn Val Leu
            100                 105                 110

Ile Asp Asp Asp Gly Val Ala Leu Arg Gly Thr Phe Val Ile Asn Pro
        115                 120                 125

Glu Gly Val Ile Lys Leu Cys Glu Ile His Asp Leu Gly Ile Gly Arg
    130                 135                 140

Ser Ala Thr Glu Leu Leu Arg Lys Val Gln Ala Ala Gln Tyr Val Ala
145                 150                 155                 160

Thr His Lys Gly Gln Val Cys Pro Ala Ser Trp Gln Pro Gly Ala Glu
                165                 170                 175

Thr Leu Ala Pro Ser Leu Asp Leu Val Gly Lys Ile
            180                 185

<210> SEQ ID NO 9
<211> LENGTH: 428
<212> TYPE: PRT
<213> ORGANISM: Oxalobacter formigenes

<400> SEQUENCE: 9

Met Thr Lys Pro Leu Asp Gly Ile Asn Val Leu Asp Phe Thr His Val
1               5                   10                  15

Gln Ala Gly Pro Ala Cys Thr Gln Met Met Gly Phe Leu Gly Ala Asn
            20                  25                  30

Val Ile Lys Ile Glu Arg Arg Gly Ser Gly Asp Met Thr Arg Gly Trp
        35                  40                  45

Leu Gln Asp Lys Pro Asn Val Asp Ser Leu Tyr Phe Thr Met Phe Asn
    50                  55                  60
```

```
Cys Asn Lys Arg Ser Ile Glu Leu Asp Met Lys Thr Pro Glu Gly Lys
 65                  70                  75                  80

Glu Leu Leu Glu Gln Met Ile Lys Lys Ala Asp Val Met Val Glu Asn
                 85                  90                  95

Phe Gly Pro Gly Ala Leu Asp Arg Met Gly Phe Thr Trp Glu Tyr Ile
            100                 105                 110

Gln Glu Leu Asn Pro Arg Val Ile Leu Ala Ser Val Lys Gly Tyr Ala
        115                 120                 125

Glu Gly His Ala Asn Glu His Leu Lys Val Tyr Glu Asn Val Ala Gln
    130                 135                 140

Cys Ser Gly Gly Ala Ala Thr Thr Gly Phe Trp Asp Gly Pro Pro
145                 150                 155                 160

Thr Val Ser Gly Ala Ala Leu Gly Asp Ser Asn Ser Gly Met His Leu
                165                 170                 175

Met Ile Gly Ile Leu Ala Ala Leu Glu Ile Arg His Lys Thr Gly Arg
            180                 185                 190

Gly Gln Lys Val Ala Val Ala Met Gln Asp Ala Val Leu Asn Leu Val
        195                 200                 205

Arg Ile Lys Leu Arg Asp Gln Gln Arg Leu Glu Arg Thr Gly Ile Leu
210                 215                 220

Ala Glu Tyr Pro Gln Ala Gln Pro Asn Phe Ala Phe Asp Arg Asp Gly
225                 230                 235                 240

Asn Pro Leu Ser Phe Asp Asn Ile Thr Ser Val Pro Arg Gly Gly Asn
                245                 250                 255

Ala Gly Gly Gly Gly Gln Pro Gly Trp Met Leu Lys Cys Lys Gly Trp
            260                 265                 270

Glu Thr Asp Ala Asp Ser Tyr Val Tyr Phe Thr Ile Ala Ala Asn Met
        275                 280                 285

Trp Pro Gln Ile Cys Asp Met Ile Asp Lys Pro Glu Trp Lys Asp Asp
    290                 295                 300

Pro Ala Tyr Asn Thr Phe Glu Gly Arg Val Asp Lys Leu Met Asp Ile
305                 310                 315                 320

Phe Ser Phe Ile Glu Thr Lys Phe Ala Asp Lys Asp Lys Phe Glu Val
                325                 330                 335

Thr Glu Trp Ala Ala Gln Tyr Gly Ile Pro Cys Gly Pro Val Met Ser
            340                 345                 350

Met Lys Glu Leu Ala His Asp Pro Ser Leu Gln Lys Val Gly Thr Val
        355                 360                 365

Val Glu Val Val Asp Glu Ile Arg Gly Asn His Leu Thr Val Gly Ala
    370                 375                 380

Pro Phe Lys Phe Ser Gly Phe Gln Pro Glu Ile Thr Arg Ala Pro Leu
385                 390                 395                 400

Leu Gly Glu His Thr Asp Glu Val Leu Lys Glu Leu Gly Leu Asp Asp
                405                 410                 415

Ala Lys Ile Lys Glu Leu His Ala Lys Gln Val Val
            420                 425
```

<210> SEQ ID NO 10
<211> LENGTH: 353
<212> TYPE: PRT
<213> ORGANISM: Oxalobacter formigenes

<400> SEQUENCE: 10

```
Met Asp Thr Thr Asp Asp Leu Arg Ile Leu Ala Met Lys Glu Leu Thr
  1               5                  10                  15
```

Pro Pro Ala His Leu Ile Arg Glu Phe Pro Cys Glu Lys Ala Ala
            20                  25                  30

Glu Thr Val Ser Gly Cys Arg Lys Ala Ile Gln Arg Val Leu His Asn
        35                  40                  45

Gln Asp Asp Arg Leu Val Val Ile Ile Gly Pro Cys Ser Ile His Asp
50                  55                  60

Pro Lys Ala Ala Met Glu Tyr Ala His Arg Leu Ala Glu Glu Lys Glu
65                  70                  75                  80

Arg Tyr Gly Asp Glu Leu Val Val Met Arg Val Tyr Phe Glu Lys
                85                  90                  95

Pro Arg Thr Thr Ile Gly Trp Lys Gly Leu Ile Asn Asp Pro Phe Met
            100                 105                 110

Asp His Ser Tyr Arg Ile Asn Glu Gly Leu His Ile Ala Arg Glu Leu
        115                 120                 125

Leu Arg Asp Val Asn Glu Leu Gly Leu Pro Ala Ala Thr Glu Tyr Leu
    130                 135                 140

Asp Met Ile Ser Pro Gln Tyr Val Ala Asp Met Ile Ser Trp Gly Ala
145                 150                 155                 160

Ile Gly Ala Arg Thr Thr Glu Ser Gln Val His Arg Glu Leu Ser Ser
                165                 170                 175

Gly Leu Ser Cys Pro Val Gly Phe Lys Asn Gly Thr Asp Gly Asn Ile
            180                 185                 190

Lys Ile Ala Ile Asp Ala Ile Lys Ala Ser His Pro His His Phe
        195                 200                 205

Leu Ser Val Thr Lys Gly Gly His Thr Ala Ile Phe Glu Thr Glu Gly
    210                 215                 220

Asn Gln Asp Cys His Ile Ile Leu Arg Gly Gly Tyr Lys Pro Asn Tyr
225                 230                 235                 240

Asp Ala Ala Ser Val Asn Glu Ala Ala Arg Ala Val Glu Ala Ala Gly
                245                 250                 255

Leu Ala Pro Lys Ile Met Ile Asp Ala Ser His Gly Asn Ser Ser Lys
            260                 265                 270

Lys Ala Glu Asn Gln Val Pro Val Ser Leu Glu Val Gly Glu Asn Ile
        275                 280                 285

Ala Lys Gly Asp Asp Arg Ile Ile Gly Leu Met Ile Glu Ser Asn Leu
    290                 295                 300

Val Gly Gly Arg Gln Asp His Glu Val Gly Lys Lys Leu Val Tyr Gly
305                 310                 315                 320

Gln Ser Val Thr Asp Ala Cys Ile Gly Trp Glu Asp Ser Ser Lys Leu
                325                 330                 335

Leu Gly Gln Leu Ala Glu Thr Val Lys Arg Arg Arg Asp Val Leu Lys
            340                 345                 350

Lys

<210> SEQ ID NO 11
<211> LENGTH: 361
<212> TYPE: PRT
<213> ORGANISM: Oxalobacter formigenes

<400> SEQUENCE: 11

Met Ser Lys Lys Phe Gly Gly Glu Ala Lys Asp Tyr Asp Gln Ile Asp
1               5                   10                  15

Ala Ala Pro Glu Glu Lys Ala Arg Gly Ile Thr Ile Asn Thr Ser His
            20                  25                  30

Val Glu Tyr Glu Thr Ala Ala Arg His Tyr Ala His Val Asp Cys Pro
         35                  40                  45

Gly His Ala Asp Tyr Ile Lys Asn Met Ile Thr Gly Ala Ala Gln Met
 50                  55                  60

Asp Gly Ala Ile Leu Val Val Ser Ala Ala Asp Gly Pro Met Pro Gln
 65                  70                  75                  80

Thr Arg Glu His Ile Leu Leu Ala Arg Gln Val Gly Val Pro Tyr Ile
                 85                  90                  95

Ile Val Phe Leu Asn Lys Cys Asp Met Val Asp Asp Ala Glu Leu Leu
             100                 105                 110

Glu Leu Val Glu Met Glu Val Arg Glu Leu Leu Ser Arg Tyr Glu Phe
             115                 120                 125

Pro Gly Asp Asp Ile Pro Ile Ile Lys Gly Ser Ala Lys Leu Ala Leu
         130                 135                 140

Glu Gly Asp Ala Gly Glu Leu Gly Glu Thr Ala Ile Leu Ala Leu Ala
145                 150                 155                 160

Asp Ala Leu Asp Ser Tyr Ile Pro Thr Pro Glu Arg Ala Val Asp Gly
                 165                 170                 175

Ala Phe Leu Met Pro Val Glu Asp Val Phe Ser Ile Ser Gly Arg Gly
             180                 185                 190

Thr Val Val Thr Gly Arg Val Glu Arg Gly Ile Ile Lys Val Gly Glu
             195                 200                 205

Glu Ile Glu Ile Val Gly Ile Lys Glu Thr Ala Lys Thr Thr Cys Thr
210                 215                 220

Gly Val Glu Met Phe Arg Lys Leu Leu Asp Gln Gly Gln Ala Gly Asp
225                 230                 235                 240

Asn Ile Gly Val Leu Leu Arg Gly Thr Lys Arg Glu Glu Val Glu Arg
                 245                 250                 255

Gly Gln Val Leu Ala Lys Pro Gly Ser Ile Lys Pro His Leu Asn Phe
             260                 265                 270

Glu Gly Glu Val Tyr Val Leu Ser Lys Glu Glu Gly Gly Arg His Thr
             275                 280                 285

Pro Phe Phe Asn Asn Tyr Arg Pro Gln Phe Tyr Phe Arg Thr Thr Asp
         290                 295                 300

Val Thr Gly Ala Ile Glu Leu Pro Lys Asp Lys Glu Met Val Met Pro
305                 310                 315                 320

Gly Asp Asn Val Ser Ile Ser Val Lys Leu Ile Ser Pro Ile Ala Met
                 325                 330                 335

Glu Glu Gly Leu Arg Phe Ala Ile Arg Glu Gly Arg Thr Val Gly
             340                 345                 350

Ala Gly Val Val Ala Lys Ile Thr Glu
         355                 360

<210> SEQ ID NO 12
<211> LENGTH: 470
<212> TYPE: PRT
<213> ORGANISM: Oxalobacter formigenes

<400> SEQUENCE: 12

Met Asn Ala Val Ser Lys Thr Glu Gln Asp Phe Tyr Ile Ala Asp Pro
  1               5                  10                  15

Asp Leu Thr Ala Trp Gly Asn Lys Glu Ile Arg Ile Ala Glu Thr Glu
             20                  25                  30

Met Pro Gly Leu Met Ala Ile Arg Glu Glu Tyr Ala Ala Ser Lys Pro

```
            35                  40                  45
Leu Ser Gly Ala Arg Ile Ser Gly Ser Leu His Met Thr Ile Gln Thr
 50                  55                  60

Ala Val Leu Ile Gln Thr Leu Glu Ala Leu Gly Ala Lys Val Arg Trp
 65                  70                  75                  80

Ala Ser Cys Asn Ile Tyr Ser Thr Gln Asp His Ala Ala Ala Ala Ile
                 85                  90                  95

Ala Ser Asn Gly Thr Pro Val Phe Ala Phe Lys Gly Glu Ser Leu Asp
                100                 105                 110

Asp Tyr Trp Glu Phe Thr His Arg Ile Phe Glu Trp Pro Asp Gly Gly
                115                 120                 125

Tyr Ser Asn Met Ile Leu Asp Asp Gly Gly Asp Ala Thr Leu Leu Leu
                130                 135                 140

His Leu Gly Ser Arg Ala Glu Lys Asp Ala Thr Val Leu Asp Asn Pro
145                 150                 155                 160

Gly Ser Glu Glu Glu Val Cys Leu Phe Asn Ala Ile Lys Arg His Leu
                165                 170                 175

Lys Thr Asp Pro Asn Trp Tyr Ser Lys Arg Ile Lys Glu Ile Lys Gly
                180                 185                 190

Val Thr Glu Glu Thr Thr Thr Gly Val His Arg Leu Tyr Gln Met His
                195                 200                 205

Glu Glu Gly Lys Leu Lys Phe Pro Ala Ile Asn Val Asn Asp Ser Val
210                 215                 220

Thr Lys Ser Lys Phe Asp Asn Leu Tyr Gly Cys Arg Glu Ser Leu Val
225                 230                 235                 240

Asp Gly Ile Lys Arg Ala Thr Asp Val Met Ile Ala Gly Lys Val Ala
                245                 250                 255

Val Val Cys Gly Tyr Gly Asp Val Gly Lys Gly Cys Ala Gln Ala Leu
                260                 265                 270

Lys Ala Leu Ser Ala Gln Val Trp Val Thr Glu Val Asp Pro Ile Cys
                275                 280                 285

Ala Leu Gln Ala Ala Met Glu Gly Tyr Arg Val Val Thr Met Asp Tyr
                290                 295                 300

Ala Ala Glu Met Ala Asp Ile Phe Val Thr Cys Thr Gly Asn Tyr His
305                 310                 315                 320

Val Ile Thr His Asp His Met Val Lys Met Lys Asp Gln Ala Ile Val
                325                 330                 335

Cys Asn Ile Gly His Phe Asp Asn Glu Ile Asp Val Ala Ser Met Lys
                340                 345                 350

Lys Tyr Thr Trp Asp Asn Ile Lys Pro Gln Val Asp His Ile Ile Leu
                355                 360                 365

Pro Asn Gly Asn Arg Ile Ile Leu Leu Ala Glu Gly Arg Leu Val Asn
                370                 375                 380

Leu Gly Cys Gly Thr Gly His Pro Ser Tyr Val Met Ser Ser Ser Phe
385                 390                 395                 400

Ala Asn Gln Thr Ile Ala Gln Ile Glu Leu Phe Thr Asn Thr Glu Ala
                405                 410                 415

Tyr Pro Val Gly Val Tyr Thr Leu Pro Lys His Leu Asp Glu Lys Val
                420                 425                 430

Ala Arg Leu Gln Leu Lys Lys Leu Asn Ala Val Leu Thr Glu Leu Ser
                435                 440                 445

Asp Glu Gln Ala Ala Tyr Ile Gly Val Lys Lys Glu Gly Pro Tyr Lys
450                 455                 460
```

Pro Asn His Tyr Arg Tyr
465                 470

<210> SEQ ID NO 13
<211> LENGTH: 255
<212> TYPE: PRT
<213> ORGANISM: Oxalobacter formigenes

<400> SEQUENCE: 13

Met Ala Asn Gln Glu Glu Pro Ile Lys Val Thr Asp Asp Phe Lys Gln
1               5                   10                  15

Cys Trp Gln Ser Ala Gly Arg His Leu Gln Ser Gln Val Glu Gly Gly
            20                  25                  30

Leu Thr Trp Met Arg Ala Ser Leu Asp Glu Pro Phe Met Glu His Leu
        35                  40                  45

Ser Phe Arg Leu Gly Asn Gln Leu Phe Phe Val Arg Val Ile Asp Val
    50                  55                  60

Asp Asn Glu Leu Lys Val Pro Gly Thr Asp Glu Asn Leu Ile Lys Ile
65                  70                  75                  80

Ala Glu Gly Cys Lys Gly His Ala Cys Ile Met Pro Met Arg Phe Ser
                85                  90                  95

Phe Gly Asn Trp Met Pro Val Glu Lys Gly Trp Gly Leu Leu Ser Ala
            100                 105                 110

Val Asp Lys Lys Pro Val Asn Pro Asp Leu Val Thr Asp Glu Lys
        115                 120                 125

Ile Glu Met Thr Asp Trp Glu Leu His Asp Phe Ala Val Gln Val Val
    130                 135                 140

Arg Gln Asn Leu Met His Glu Gly His Val Ala Gly Trp Val Ser
145                 150                 155                 160

Asn Pro Glu Leu Gln Pro Ser Ile Trp Ile Ser Thr Glu Glu Phe Pro
                165                 170                 175

Gln Trp Val Val Val Gln Ala Val Arg Trp Pro Ala Glu Ala Lys Ile
            180                 185                 190

Pro Asp Asn Ile Lys Glu Ile Glu Asp Ala Tyr Ala Ser Lys Glu Ala
        195                 200                 205

Lys Gly Thr Phe Ala Tyr Val Thr Phe Ala Asn Glu Asn Gln Asn Val
    210                 215                 220

Lys Glu Pro Leu Lys Glu Gly Glu Lys Pro Leu Pro Ile Tyr Arg Gly
225                 230                 235                 240

Asp Lys Ala Tyr Ile Ser Tyr Ser Gly Leu Leu Ser Thr Glu Asn
                245                 250                 255

<210> SEQ ID NO 14
<211> LENGTH: 307
<212> TYPE: PRT
<213> ORGANISM: Oxalobacter formigenes

<400> SEQUENCE: 14

Met Thr Thr Ile Lys Ala Ala Val His Gly Leu Gly Asn Ile Gly Arg
1               5                   10                  15

His Val Ile Asp Cys Leu Thr Cys Ala Pro Asp Phe Glu Cys Leu Gly
            20                  25                  30

Val Ile Arg Arg Glu Ser Ser Leu Gly Thr Gln Thr Leu Glu Arg Arg
        35                  40                  45

Asn Ile Pro Asp Tyr Ala Ser Ile Asp Lys Leu Ile Ala Glu Lys Gly
    50                  55                  60

Lys Pro Asp Val Val Ile Leu Cys Gly Pro Ser Arg Ser Val Pro Glu
65                  70                  75                  80

Asp Ala Lys Phe Tyr Leu Ser Arg Gly Ile Arg Thr Val Asp Ser Phe
                85                  90                  95

Asp Ile His Thr Asp Ile Ala Glu Leu Val Glu Lys Leu Asp Val Val
            100                 105                 110

Ala Lys Glu Asn Asn Ser Ala Cys Ile Thr Ala Ala Gly Trp Asp Pro
        115                 120                 125

Gly Thr Asp Ser Val Phe Arg Thr Leu Phe Glu Ala Met Ala Pro Thr
    130                 135                 140

Gly Thr Thr Phe Thr Asn Phe Gly Arg Gly Arg Ser Met Gly His Ser
145                 150                 155                 160

Val Ala Ala Arg Ala Ile Lys Gly Val Ala Asp Ala Thr Ser Ile Thr
                165                 170                 175

Ile Pro Ile Gly Gly Gly Arg His Ala Arg Leu Val Tyr Val Leu Ala
            180                 185                 190

Glu Lys Gly Ala Ser Phe Glu Gln Ile Lys Lys Asp Leu Ala Ser Asp
        195                 200                 205

Pro Tyr Phe Ser His Asp Pro Leu Asp Val Arg Glu Val Lys Thr Pro
    210                 215                 220

Glu Glu Met Glu Ala Val Ala Asp Asn Ser His Gly Val Leu Met Glu
225                 230                 235                 240

Arg Ile Gly Ala Ser Gly Arg Thr Ser Asn Gln Asn Leu Thr Phe Thr
                245                 250                 255

Met Lys Ile Asp Asn Pro Ala Leu Thr Ser Gln Val Leu Val Ser Cys
            260                 265                 270

Ala Arg Ala Val Thr Arg Met Gly Ala Gly Cys His Thr Leu Ile Asp
        275                 280                 285

Val Pro Pro Val Met Leu Leu Ala Gly Glu Arg Met Gln His Ile Ala
    290                 295                 300

Arg Leu Val
305

<210> SEQ ID NO 15
<211> LENGTH: 415
<212> TYPE: PRT
<213> ORGANISM: Oxalobacter formigenes

<400> SEQUENCE: 15

Met Phe Ala Lys Asp Tyr Ser Leu Ala Gln Val Asp Ser Glu Leu Trp
1               5                   10                  15

Asp Ala Ile Leu Arg Glu Asn Thr Arg Gln Glu Glu His Ile Glu Leu
            20                  25                  30

Ile Ala Ser Glu Asn Tyr Cys Ser Pro Ala Val Met Gln Ala Gln Gly
        35                  40                  45

Ser Gln Leu Thr Asn Lys Tyr Ala Glu Gly Tyr Pro Gly Lys Arg Tyr
    50                  55                  60

Tyr Gly Gly Cys Glu Tyr Val Asp Ile Ala Glu Gln Leu Ala Leu Asp
65                  70                  75                  80

Arg Val Lys Lys Leu Phe Gly Ala Glu Ala Ala Asn Val Gln Pro Asn
                85                  90                  95

Ser Gly Ser Gln Ala Asn Gln Ala Ile Phe Leu Ala Met Leu Asn Pro
            100                 105                 110

Gly Asp Thr Ile Met Gly Met Ser Leu Ala Glu Gly Gly His Leu Thr

```
                115                 120                 125
        His Gly Met Ala Leu Asn Met Ser Gly Lys Trp Phe Asn Val Val Ser
            130                 135                 140

Tyr Gly Leu Asn Glu Lys Glu Ile Asp Tyr Asp Arg Met Glu Gln
    145                 150                 155                 160

Leu Ala His Glu His Lys Pro Lys Leu Ile Ala Gly Ala Ser Ala
                        165                 170                 175

Tyr Ser Leu Arg Ile Asp Phe Glu Arg Phe Ala Lys Val Ala Arg Asp
                    180                 185                 190

Val Gly Ala Phe Phe Met Val Asp Met Ala His Tyr Ala Gly Leu Ile
                195                 200                 205

Ala Ala Gly Val Tyr Pro Ser Pro Val Pro Tyr Ala Asp Phe Val Thr
            210                 215                 220

Ser Thr Thr His Lys Ser Leu Arg Gly Pro Arg Gly Phe Ile Leu
    225                 230                 235                 240

Met Lys Pro Glu Phe Glu Arg Lys Ile Asn Ser Ala Val Phe Pro Gly
                        245                 250                 255

Leu Gln Gly Gly Pro Leu Met His Val Ile Ala Gly Lys Ala Val Ala
                    260                 265                 270

Phe Lys Glu Ala Leu Gln Pro Glu Phe Lys Thr Tyr Gln Glu Val
                275                 280                 285

Leu Lys Asn Ala Ser Val Leu Ala Lys Thr Leu Val Asp Arg Gly Phe
            290                 295                 300

Arg Ile Ile Ser Gly Arg Thr Glu Ser His Val Met Leu Val Asp Leu
    305                 310                 315                 320

Gln Ser Lys Asn Ile Thr Gly Arg Gln Ala Glu Thr Ile Leu Asn Ser
                        325                 330                 335

Gly His Ile Thr Cys Asn Lys Asn Ala Ile Pro Asn Asp Pro Gln Thr
                    340                 345                 350

Pro Phe Val Thr Ser Gly Val Arg Leu Gly Ser Pro Ala Met Thr Thr
                355                 360                 365

Arg Gly Phe Lys Glu Thr Glu Ser Ala Ile Val Gly Asn Leu Leu Ala
            370                 375                 380

Asp Val Ile Glu Asn Pro Asn Asp Gln Ala Thr Ile Glu Arg Val Arg
    385                 390                 395                 400

Ala Glu Val Lys Lys Leu Thr Thr Ala Phe Pro Val Tyr Gln His
                        405                 410                 415

<210> SEQ ID NO 16
<211> LENGTH: 371
<212> TYPE: PRT
<213> ORGANISM: Oxalobacter formigenes

<400> SEQUENCE: 16

Met Lys Leu Val Gly Leu Ile Gly Trp Arg Gly Met Val Gly Ser Val
    1               5                   10                  15

Leu Met Gln Arg Met Gln Glu Glu Asn Asp Phe Asp Leu Phe Glu Pro
                        20                  25                  30

Val Phe Phe Thr Thr Ser Asn Val Gly Gly Lys Ala Pro Ala Met Ala
                    35                  40                  45

Lys Asn Glu Thr Val Leu Lys Asp Ala Phe Asn Ile Asp Glu Leu Lys
                50                  55                  60

Lys Cys Asp Ile Leu Ile Ser Cys Gln Gly Gly Asp Tyr Thr Val Asp
    65                  70                  75                  80
```

Val Phe Pro Lys Leu Arg Ala Ala Gly Trp Asp Gly Tyr Trp Ile Asp
            85                  90                  95

Ala Ala Ser Lys Leu Arg Met Asn Asp Asp Ala Leu Ile Ile Leu Asp
        100                 105                 110

Pro Val Asn Arg Lys Val Ile Glu Asp Gly Leu Ser Lys Gly Ile Lys
        115                 120                 125

Asn Tyr Ile Gly Gly Asn Cys Thr Val Ser Cys Met Leu Met Gly Leu
    130                 135                 140

Gly Gly Leu Phe Glu Asn Asp Leu Val Glu Trp Met Thr Ser Met Thr
145                 150                 155                 160

Tyr Gln Ala Ala Ser Gly Gly Ala Gln His Met Arg Glu Leu Leu
                165                 170                 175

Thr Gln Phe Gly Ser Ile His Thr Glu Val Arg Met Asn Leu Glu Asn
        180                 185                 190

Pro Ala Ser Ala Ile Leu Glu Ile Asp Arg Gln Val Leu Ala Arg Gln
        195                 200                 205

Arg Gly Met Thr Ala Asp Glu Thr Lys Gln Phe Gly Val Pro Leu Ala
    210                 215                 220

Gly Asn Leu Ile Pro Trp Ile Asp Thr Asp Leu Gly Asn Gly Met Ser
225                 230                 235                 240

Arg Glu Glu Trp Lys Gly Gly Ala Glu Thr Asn Lys Ile Leu Gly Lys
                245                 250                 255

Asn Asp Gly Asn Lys Val Ile Val Asp Gly Leu Cys Val Arg Val Gly
        260                 265                 270

Ala Met Arg Cys His Ser Gln Ala Leu Thr Ile Lys Leu Lys Lys Asp
    275                 280                 285

Val Pro Leu Asp Glu Ile Thr Asp Ile Leu Lys Ser His Asn Gln Trp
    290                 295                 300

Ala Lys Val Val Pro Asn Thr Lys Glu Asp Ser Val Arg Asp Leu Thr
305                 310                 315                 320

Pro Ala Ala Val Ser Gly Ser Leu Thr Ile Pro Val Gly Arg Leu Arg
                325                 330                 335

Lys Leu Glu Met Gly Asn Asp Tyr Leu Ser Ala Phe Thr Val Gly Asp
            340                 345                 350

Gln Leu Leu Trp Gly Ala Ala Glu Pro Leu Arg Arg Met Leu Arg Ile
            355                 360                 365

Ile Leu Glu
    370

<210> SEQ ID NO 17
<211> LENGTH: 429
<212> TYPE: PRT
<213> ORGANISM: Oxalobacter formigenes

<400> SEQUENCE: 17

Met Asn Ser Gln Asp Gln Lys Lys Glu Leu Leu Lys Lys Asn Ala Leu
1               5                   10                  15

Ala Phe His Arg Phe Pro Ile Pro Gly Lys Ile Ser Val Asn Pro Thr
            20                  25                  30

Lys Glu Val Arg Asp Gln Asn Glu Leu Ala Leu Ala Tyr Thr Pro Gly
        35                  40                  45

Val Ala Cys Ala Cys Glu Glu Ile His Ala Asn Pro Glu Asn Ala Tyr
    50                  55                  60

Ile Tyr Thr Thr Lys Gly Asn Leu Val Ala Val Ile Ser Asn Gly Thr
65                  70                  75                  80

Ala Val Leu Gly Leu Gly Asn Ile Gly Ala Gln Ala Ser Lys Pro Val
                        85                  90                  95

Met Glu Gly Lys Gly Val Leu Phe Lys Lys Phe Ala Asp Ile Asn Val
                100                 105                 110

Phe Asp Leu Glu Ile Asn Glu Leu Asp Pro Asp Lys Leu Cys Asp Ile
            115                 120                 125

Ile Ala Ser Leu Glu Pro Thr Phe Gly Ile Asn Leu Glu Asp Ile
130                 135                 140

Arg Ala Pro Glu Cys Phe Tyr Ile Glu Arg Lys Leu Arg Glu Lys Met
145                 150                 155                 160

Asn Ile Pro Val Phe His Asp Asp Gln His Gly Thr Ala Val Ile Val
                165                 170                 175

Gly Ala Ala Val Leu Asn Ala Leu Lys Val Val Gly Lys Asn Ile Lys
                180                 185                 190

Asn Cys Lys Met Val Val Ser Gly Ala Gly Ala Gly Ala Met Gly Cys
                195                 200                 205

Leu Glu Leu Leu Val Asp Leu Gly Phe Pro Val Glu Asn Ile Trp Val
        210                 215                 220

Thr Asp Ile Lys Gly Val Val Tyr Lys Gly Arg Lys Glu Leu Met Asp
225                 230                 235                 240

Pro Glu Lys Glu Lys Tyr Ala Gln Glu Thr Asp Ala Arg Thr Leu Met
                245                 250                 255

Asp Val Ile Ser Asp Ala Asp Ile Phe Leu Gly Leu Ser Ala Gly Asn
                260                 265                 270

Val Leu Lys Pro Glu Met Val Leu Lys Met Ala Lys Asp Pro Val Ile
            275                 280                 285

Phe Ala Met Ala Asn Pro Ile Pro Glu Ile Leu Pro Glu Val Ala His
290                 295                 300

Ala Thr Arg Asp Asp Val Ile Met Gly Thr Gly Arg Ser Asp Tyr Pro
305                 310                 315                 320

Asn Gln Ile Asn Asn Ser Met Cys Phe Pro Tyr Leu Phe Arg Gly Ala
                325                 330                 335

Leu Asp Cys Arg Ala Lys Thr Ile Asn Arg Glu Met Glu Leu Ala Ala
                340                 345                 350

Val Arg Ala Ile Ala Ser Leu Ala Glu Met Glu Cys Pro Glu Glu Ile
            355                 360                 365

Val Ala Met Tyr Gly Lys Lys Tyr Thr Phe Gly Arg Asp Tyr Leu Leu
        370                 375                 380

Pro Phe Gln Phe Asp Pro Arg Leu Leu Trp Val Ala Pro Ala Val
385                 390                 395                 400

Ala Gln Ala Ala Met Asp Ser Gly Val Ala Arg Val Gln Ile Ala Asp
                405                 410                 415

Met Asp Ala Tyr Arg Ala Lys Leu Lys Glu Phe Val Gly
            420                 425

<210> SEQ ID NO 18
<211> LENGTH: 907
<212> TYPE: PRT
<213> ORGANISM: Oxalobacter formigenes

<400> SEQUENCE: 18

Met Ser Cys Phe Thr Gln Asn Thr Tyr Lys Glu Phe Pro Val Thr His
1               5                   10                  15

Glu Lys Lys Gly His Phe Tyr Ser Ile Pro Ala Leu Gly Lys Glu Leu

```
                20                  25                  30
Gly Leu Asp Leu Ser Arg Leu Pro Val Ser Ile Arg Ile Val Leu Glu
            35                  40                  45
Ser Val Leu Arg Asn Cys Asp Gly Lys Lys Ile Thr Glu Glu His Val
         50                  55                  60
Arg Gln Leu Ala Asn Trp Lys Pro Asn Glu Glu Arg Ser Asn Glu Ile
 65                  70                  75                  80
Pro Phe Val Val Ala Arg Val Ile Leu Gln Asp Phe Thr Gly Ile Pro
                 85                  90                  95
Leu Leu Val Asp Leu Ala Ala Met Arg Asn Val Ala Val Lys Thr Gly
                100                 105                 110
Lys Asn Pro Lys Lys Ile Glu Pro Leu Val Pro Val Asp Leu Val Val
            115                 120                 125
Asp His Ser Val Gln Ile Asp Tyr Phe Arg Gln Asp Asn Ala Leu Asp
         130                 135                 140
Leu Asn Met Lys Leu Glu Phe Asp Arg Asn Arg Glu Arg Tyr Gln Phe
145                 150                 155                 160
Met Lys Trp Gly Met Gln Ala Phe Asp Thr Phe Gly Val Val Pro Pro
                165                 170                 175
Gly Phe Gly Ile Val His Gln Val Asn Met Glu Tyr Leu Ala Arg Gly
                180                 185                 190
Val His Lys Arg Asn Asp Ala Glu Ala Gly Asp Val Tyr Tyr Pro Asp
            195                 200                 205
Thr Leu Val Gly Thr Asp Ser His Thr Thr Met Ile Asn Gly Val Gly
         210                 215                 220
Val Val Gly Trp Gly Val Gly Gly Ile Glu Ala Glu Ala Gly Met Leu
225                 230                 235                 240
Gly Gln Pro Val Tyr Phe Leu Thr Pro Asp Val Ile Gly Met Asn Leu
                245                 250                 255
Thr Gly Lys Leu Arg Glu Gly Cys Thr Ala Thr Asp Leu Val Leu Thr
                260                 265                 270
Ile Thr Glu Leu Leu Arg Lys Glu Lys Val Val Gly Lys Phe Val Glu
            275                 280                 285
Phe Phe Gly Glu Gly Ala Ala Ser Leu Ser Ala Thr Asp Arg Ala Thr
         290                 295                 300
Ile Ala Asn Met Ala Pro Glu Tyr Gly Ala Thr Ile Gly Phe Phe Thr
305                 310                 315                 320
Val Asp Glu Ala Thr Ile Ser Tyr Phe Lys Asn Thr Gly Arg Thr Asp
                325                 330                 335
Glu Glu Val Ser Ala Leu Glu Ser Tyr Phe Arg Ala Gln Gly Met Phe
            340                 345                 350
Gly Ile Pro Lys Ala Gly Gln Ile Asp Tyr Thr Arg Val Val Asn Leu
         355                 360                 365
Asp Leu Gly Ser Val Thr Ala Ser Val Ser Gly Pro Arg Arg Pro Gln
         370                 375                 380
Asp Arg Ile Glu Leu Gly Asn Leu Lys Lys Arg Phe Thr Glu Leu Phe
385                 390                 395                 400
Ser Ala Pro Val Lys Asp Gly Gly Phe Asn Lys Lys Pro Ala Asp Met
                405                 410                 415
Glu Ala Thr Tyr Val Asn Ser Asp Asn Val Glu Leu Lys Asn Gly Asp
            420                 425                 430
Ile Leu Ile Ala Ala Ile Thr Ser Cys Thr Asn Thr Ser Asn Pro Ala
         435                 440                 445
```

```
Val Leu Leu Ala Ala Gly Leu Ala Lys Lys Ala Val Glu Ala Gly
    450                 455                 460

Leu Gln Val Ser Pro Arg Ile Lys Thr Ser Leu Ala Pro Gly Ser Arg
465                 470                 475                 480

Ile Val Thr Asn Tyr Leu Glu Lys Ala Gly Leu Leu Pro Tyr Leu Glu
                485                 490                 495

Lys Leu Gly Phe Asn Val Ala Ala Tyr Gly Cys Thr Thr Cys Ile Gly
                500                 505                 510

Asn Ala Gly Asp Leu Thr Pro Ala Met Asn Glu Ala Ile Val Lys Asn
            515                 520                 525

Asp Val Ala Ala Ala Val Leu Ser Gly Asn Arg Asn Phe Glu Ala
    530                 535                 540

Arg Ile His Pro Asn Ile Arg Ala Asn Phe Leu Ala Ser Pro Pro Leu
545                 550                 555                 560

Val Val Ala Tyr Ala Ile Ala Gly Asn Val Thr Arg Asp Leu Thr Thr
                565                 570                 575

Glu Pro Leu Gly Lys Gly Lys Asp Gly Lys Asp Ile Tyr Leu Ser Asp
            580                 585                 590

Ile Trp Pro Thr Ser His Glu Val Ala Ala Leu Val Pro Leu Ala Leu
    595                 600                 605

Asp Ala Pro Ser Phe Arg Lys Asn Tyr Ser Asp Ile Lys Thr Ala Pro
610                 615                 620

Gly Glu Leu Trp Gln Lys Ile Ala Gly Phe Ala Thr Gly Asp Val Tyr
625                 630                 635                 640

Asp Trp Pro Gln Ser Thr Tyr Ile Ala Glu Pro Pro Phe Phe Ser Asp
                645                 650                 655

Phe Gly Met Glu Pro Asn Ala Ala Ser Ala Asn Ile Ser Gly Ala Arg
            660                 665                 670

Ala Leu Ala Leu Phe Gly Asp Ser Ile Thr Thr Asp His Ile Ser Pro
    675                 680                 685

Ala Gly Ser Ile Gln Glu Lys Ser Pro Ala Gly Gln Trp Leu Met Glu
690                 695                 700

His Gly Ile Ser Lys Ala Asn Phe Asn Ser Phe Gly Ser Arg Arg Gly
705                 710                 715                 720

Asn His Glu Val Met Met Arg Gly Thr Phe Gly Asn Val Arg Ile Lys
                725                 730                 735

Asn Gln Met Leu Pro Val Gly Pro Asp Gly Ser Arg Arg Glu Gly Gly
            740                 745                 750

Tyr Thr Leu Tyr Gln Pro Gly Gly Glu Glu Thr Ser Ile Phe Asp Ala
    755                 760                 765

Ala Met Arg Tyr Gln Lys Glu Asn Val Pro Thr Ile Val Ile Gly Gly
770                 775                 780

Glu Glu Tyr Gly Thr Gly Ser Ser Arg Asp Trp Ala Ala Lys Gly Thr
785                 790                 795                 800

Gln Leu Leu Gly Val Lys Ala Val Ile Ala Arg Ser Phe Glu Arg Ile
                805                 810                 815

His Arg Ser Asn Leu Val Gly Met Ala Val Leu Pro Leu Gln Phe Thr
            820                 825                 830

Gly Asn Asp Ser Ala Glu Ser Leu Gly Leu Lys Gly Asp Glu Thr Phe
    835                 840                 845

Asp Leu Thr Gly Leu Asp Asp Ile Thr Pro Leu Gln Asp Val Thr Leu
850                 855                 860
```

Val Val His Arg Ala Asp Gly Thr Thr Gln Asn Val Pro Leu Leu Leu
865                 870                 875                 880

Arg Ile Asp Thr Pro Ile Glu Val Asp Tyr Tyr Arg His Gly Gly Ile
                885                 890                 895

Leu Pro Phe Val Leu Arg Gln Leu Leu Ser Asn
            900                 905

<210> SEQ ID NO 19
<211> LENGTH: 648
<212> TYPE: PRT
<213> ORGANISM: Oxalobacter formigenes

<400> SEQUENCE: 19

Met Ser Lys Ile Ile Gly Ile Asp Leu Gly Thr Thr Asn Ser Cys Val
1               5                   10                  15

Ala Ile Ile Glu Gly Ser Gln Pro Arg Val Val Glu Asn Ser Glu Gly
            20                  25                  30

Asn Arg Thr Thr Pro Ser Val Ile Ala Tyr Leu Asp Asp Gly Glu Ile
        35                  40                  45

Leu Val Gly Ala Pro Ala Lys Arg Gln Ala Val Thr Asn Pro Lys Asn
50                  55                  60

Thr Leu Tyr Ala Ile Lys Arg Leu Ile Gly Arg Lys Phe Asp Asp Lys
65                  70                  75                  80

Glu Val Gln Arg Asp Ile Pro Ile Met Pro Phe Ser Ile Ile Lys Ala
                85                  90                  95

Glu Asn Asn Asp Ala Trp Val Ser Val Leu Asn Asp Lys Lys Leu Ala
            100                 105                 110

Pro Pro Gln Val Ser Ala Glu Val Leu Arg Lys Met Lys Lys Thr Ala
        115                 120                 125

Glu Asp Tyr Leu Gly Glu Val Thr Glu Ala Val Ile Thr Val Pro
130                 135                 140

Ala Tyr Phe Asn Asp Ala Gln Arg Gln Ala Thr Lys Asp Ala Gly Arg
145                 150                 155                 160

Ile Ala Gly Leu Asp Val Lys Arg Ile Ile Asn Glu Pro Thr Ala Ala
                165                 170                 175

Ala Leu Ala Phe Gly Leu Asp Lys Ala Gly Lys Gly Asp Lys Lys Ile
            180                 185                 190

Ala Val Tyr Asp Leu Gly Gly Gly Thr Phe Asp Ile Ser Ile Ile Glu
        195                 200                 205

Ile Ala Asp Leu Asp Gly Asp Lys Gln Phe Glu Val Leu Ser Thr Asn
210                 215                 220

Gly Asp Thr Phe Leu Gly Gly Glu Asp Phe Asp Gln Arg Ile Ile Asp
225                 230                 235                 240

Phe Ile Ile Asp Glu Phe Asn Lys Ile Asn Gly Ile Asp Leu Lys Lys
                245                 250                 255

Asp Pro Ile Ala Leu Gln Arg Ile Lys Ala Ser Ala Glu Arg Ala Lys
            260                 265                 270

Ile Glu Leu Ser Ser Ser Gln Gln Thr Glu Ile Asn Glu Pro Tyr Ile
        275                 280                 285

Ala Met Ala Asn Gly Ala Pro Val His Leu Asn Met Lys Leu Thr Arg
290                 295                 300

Ala Lys Leu Glu Ser Leu Ala Glu Gly Leu Ile Asp Gln Thr Ile Glu
305                 310                 315                 320

Pro Cys Arg Ile Ala Leu Lys Asp Ala Gly Leu Ser Val Ser Asp Ile
                325                 330                 335

-continued

```
Asp Asp Val Ile Leu Val Gly Gly Met Thr Arg Met Pro Ala Val Gln
            340             345             350
Asp Lys Val Lys Ala Phe Phe Gly Lys Glu Pro Arg Lys Asp Ile Asn
            355             360             365
Pro Asp Glu Ala Val Ala Val Gly Ala Ala Leu Gln Gly Ala Val Leu
    370             375             380
Ser Gly Asp Arg Lys Asp Leu Leu Leu Leu Asp Val Thr Pro Leu Ser
385             390             395             400
Leu Gly Ile Glu Thr Leu Gly Gly Val Met Thr Lys Met Ile Gln Lys
            405             410             415
Asn Thr Thr Ile Pro Thr Lys Phe Ser Gln Ile Phe Ser Thr Ala Glu
            420             425             430
Asp Asn Gln Pro Ala Val Thr Ile Lys Val Tyr Gln Gly Glu Arg Glu
            435             440             445
Met Ala Ala Gly Asn Lys Ala Leu Gly Glu Phe Asn Leu Glu Gly Ile
    450             455             460
Pro Ala Ser Pro Arg Gly Met Pro Gln Ile Glu Val Thr Phe Asp Ile
465             470             475             480
Asp Ala Asn Gly Ile Leu His Val Ser Ala Lys Asp Lys Ala Thr Gly
            485             490             495
Lys Glu Asn Lys Ile Thr Ile Lys Ala Asn Ser Gly Leu Ser Glu Asp
            500             505             510
Glu Ile Gln Arg Met Ile Lys Asp Ala Glu Val Asn Ala Ala Glu Asp
            515             520             525
His Lys Val Arg Glu Leu Thr Glu Ala Arg Asn Gln Gly Asp Ala Leu
            530             535             540
Val His Thr Thr Lys Lys Ser Met Glu Glu Tyr Gly Asp Lys Leu Asp
545             550             555             560
Ala Pro Ala Lys Glu Ser Ile Glu Ser Ala Ile Lys Asp Leu Glu Glu
            565             570             575
Ser Leu Lys Gly Asp Asp Lys Ala Asp Ile Asp Ser Lys Met Ser Ala
            580             585             590
Leu Ser Ala Ala Ala Gln Lys Leu Gly Glu Lys Met Tyr Ala Asp Gln
            595             600             605
Ala Pro Glu Gly Ala Ala Ala Gly Ala Ala Gly Ala Gly Ala Ser Ala
    610             615             620
Gly Ala Ala Pro Glu Pro Glu Leu Glu Asp Asp Val Val Asp Ala Asp
625             630             635             640
Phe Lys Glu Val Lys Asp Lys Asp
            645
```

SECRETAGOGUES DERIVED FROM OXALOBACTER FORMIGENES

FIELD OF THE INVENTION

The present invention relates to an identified secretagogue compound derived from oxalate degrading bacteria. The invention further relates to a method of treating a subject in need, wherein the method comprises administering a pharmaceutical composition comprising one or more secretagogues derived from oxalate degrading bacteria together with or without one or more oxalate degrading bacteria, oxalate degrading enzyme(s), enzyme(s) involved in oxalate metabolism, cofactors, substrates, or combinations thereof, to reduce the presence of oxalate in a subject. The invention also encompasses the process of manufacturing the secretagogue in sufficient quantities for identification and proposed use.

BACKGROUND OF THE INVENTION

Oxalate is the salt of a weak acid and is a metabolic end product that is excreted through the kidneys. A disrupted oxalate homeostasis in humans and animals can cause severe conditions due to the tendency of oxalate to damage the renal parenchymal cells both as free oxalate and as calcium-oxalate crystals; thus, in many cases causing irreversible damage. Oxalate homeostasis is severely disrupted due to inborn errors such as Primary Hyperoxaluria (PH).

Primary Hyperoxaluria (PH) is a rare autosomal recessive inborn error of the glyoxylate metabolism, with an incidence rate of 0.1-0.2 per million. PH type I is caused by deficient or absent activity of liver specific peroxisomal alanine/glyoxylate aminotransferase (AGT). In some patients, enzyme is present but mis-targeted to mitochondria where it is metabolically inactive.

PH type II occurs as a result of deficient glyoxylate reductase/hydroxypyruvate reductase (GRHPR) enzyme activity. Both types of PH are characterized by severe hyperoxaluria that is present from birth. Patients experience recurrent calcium-oxalate urolithiasis, nephrocalcinosis and progressive renal failure.

There are no approved therapies to treat the enzyme deficiency or enzyme dysfunction in either PH type I or PH type II. Current therapies for PH are directed to decrease oxalate production or to increase the urinary solubility of calcium oxalate in order to preserve renal function. Patients are given treatment with magnesium, citrate, and orthophosphate supplementation to increase the urinary solubility of calcium oxalate. Pyridoxine is a co-factor of the deficient AGT and pharmacological doses of pyridoxine may reduce urinary oxalate levels in a minority of patients with PH I. Eventually the only curative therapy is a combined kidney and liver transplantation.

Secondary Hyperoxaluria includes oxalate-related conditions such as, but not limited to, hyperoxaluria, absorptive hyperoxaluria, enteric hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders/conditions caused by/associated with gastrointestinal surgery, bariatric surgery (surgery for obesity), and/or antibiotic treatment. Kidney/urinary tract stone disease (urolithiasis) is a major health problem throughout the world. Most of the stones associated with urolithiasis are composed of calcium oxalate alone or calcium oxalate plus calcium phosphate.

Kidney or urinary tract stone disease occurs in as many as 12% of the population in Western countries and about 70% of these stones are composed of calcium oxalate or of calcium oxalate plus calcium phosphate. Some individuals (e.g. patients with intestinal disease such as Crohn's disease, inflammatory bowel disease, or steatorrhea and also patients that have undergone jejunoileal or Roux-en-Y bypass surgery) absorb more of the oxalate in their diets than do others. For these individuals, the incidence of oxalate urolithiasis is markedly increased.

Oxalate homeostasis is a complex process, not yet completely resolved, including many different bodily organs and mechanisms. The mammalian kidneys as well as intestinal tract act as excretion avenues, consequently lowering the oxalate concentrations within the body. However, oxalate excretion through the kidneys pose risk of toxicological effects on the renal parenchymal cells and of crystal formation in the form of kidney stones. The mammalian intestinal tract thus plays a major role in oxalate control both due to passive and active oxalate transport (Hatch and Freel, 2004; Freel et al., 2006) as well as symbiotic relationships with colonizing oxalate-degrading bacteria.

It has previously been reported that a highly concentrated lyophilized powder containing *Oxalobacter formigenes* (*O. formigenes*), a non-pathogenic, obligate anaerobic bacterium that utilizes oxalic acid as its sole source of energy, can be used to decrease oxalate in plasma and urine (U.S. Pat. Nos. 6,200,562 B1; 6,355,242 B1). The mechanism for oxalate degradation has been characterized and involves three unique proteins, an oxalate:formate membrane transporter, oxalyl-CoA decarboxylase (OXC), and formyl-CoA transferase (FRC). A very high expression of oxalate degrading proteins and their unique kinetic properties makes *O. formigenes* one of the most efficient oxalate degrading systems known.

*O. formigenes* is part of a healthy intestinal microbiota in vertebrates and as such partakes significantly in the oxalate homeostasis process. Mechanistically, *O. formigenes* increases degradation of oxalate in the gastrointestinal tract, creates a suitable transepithelial gradient, and promotes passive enteric elimination of oxalate. For the skilled artisan the importance of a balanced intestinal microbiota is well known, further, it is also known that developments in the field of microbiology have demonstrated numerous cases of bacterial secretagogue influences in the human intestine. To name a few examples; *Vibrio Cholerae* and enterotoxigenic *Escherichia coli* produce secretagogue compounds, which, briefly described, cause an efflux of ions and subsequently fluids into the intestinal lumen with the result of diarrheas (Flores, J., Sharp, G. W., 1976; Field, M., Graf, L. H., et al., 1978). Other intestinal inhabitants induce a hyper-secretion of mucin by secretagogue action (e.g. Navarro-Garcia, F., et al., 2010, Caballero-Franco, C., et al., 2006).

Recently the SLC26 (solute-linked carrier) gene family was identified (Mount, D. B., et al., *Pflugers Arch*. 2004; 447 (5):710-721; Soleimani, M., Xu, J., *Seminars in nephrology*. 2006; 26 (5):375-385). This gene family encodes for structurally related anion transporters that have a measurable oxalate affinity and are found in the GI tract: SLC26A1 (SAT1), SCL26A2 (DTDST), SLC26A3 (DRA), SLC26A6 (PAT1 or CFEX), SLC26A7, and SCL26A9. In addition, SLC26A1 and SLC26A2 have been observed in post-confluent and confluent Caco-2 monolayers, respectively (Hatch, M., et al., *NIH Oxalosis and Hyperoxaluria Workshop*, 2003; Morozumi, M., et al., *Kidney Stones: Inside & Out*. Hong Kong: 2004, Pp. 170-180). Despite these recent advancement many questions remain on the complex balance of counter ions over the epithelial membrane, the role of different oxalate transporters and what impact they have on hyperoxaluric conditions (Hassan, H. A., *Am J Physiol Cell Physiol*, 302: C46-C58, 2012; Aronson, P. S., *J Nephrol* 2010; 23 (S16): S158-S164).

Many of the transporters with oxalate affinity also demonstrate affinity for other substrates and often are linked to acid-base balances within the cells; to name a few examples: DRA expressed in *Xenopus* oocytes is a Cl⁻ base exchanger (Chernova, M. N. et al., *J Physiol*, 549:3, 2003) and studies suggests $SO_4^{2-}$ is another substrate (Byeon, M. K. et al., Protein Expr Purif, 12: 67, 1998); mouse PAT-1 expressed in *Xenopus* exhibits a variety of affinities to Cl⁻HCO₃⁻, Cl⁻Ox²⁻, $SO_4^{2-}$-Ox²⁻ (Xie Q. et al., *Am J Physiol Renal Physiol* 283: F826, 2002); and the SLC26A4 gene encodes a Cl formate exchanger (Morozumi, M. et al. In: Gohel M D I, Au D W T (eds) Kidney stones: inside and out. Hong Kong, p. 170). Many other transporters, without affinity for oxalate, have substrates in common with the oxalate transporting proteins, for example: Na⁺/K⁺ ATPase, Na⁺/H⁺ exchangers (NHEs), Na⁺—K⁺-2Cl⁻ cotransporters (NKCC), and basolateral K⁺ channels and apical Cl⁻ channels, such as the cystic fibrosis transmembrane conductance regulator (CFTR) (Venkatasubramanian, J. et al., *Curr Opin Gastroenterol*, 26: 123-128, 2010). The regulation of Na⁺, K⁺, HCO₃⁻ is highly coordinated in the intestinal tract, as it also dictates movement of water, through interactions and regulations of this multitude of transporters outlined.

Several oxalate-reducing pharmaceutical formulations have been described in the art, such as in WO2007070052 A2, Hoppe et al. (Nephrol Dial Transplant, 2011, 26: 3609-3615), and US 20050232901 A1. Among these are enteric coated or other compositions comprising oxalate degrading bacteria or enzymes that have been suggested as a means for reducing oxalate concentrations. An objective with such a treatment is for the patients to get lowered or normalized urinary oxalate levels.

Further, WO2005097176 A2 describes compositions comprising *Oxalobacter formigenes*, which can be viable and/or a lysate thereof. The compositions are useful for treating an animal subject suffering from renal failure.

SUMMARY OF THE INVENTION

The invention described herein pertains to a secretagogue component, or a secretagogue compound, derived from an oxalate degrading bacteria, which exerts a direct or indirect effect in the intestinal tract of a mammal. The effect relates to an exchange of oxalate across the intestinal epithelia in a mammal via passive flux of oxalate and/or a promotion of active transport. This invention further describes the manufacturing process for producing sufficient amounts of this secretagogue component for identification, analysis and proposed use in hyperoxaluria therapy.

Due to the complex multi-component interactions of ions and transporters in the intestinal tract, the recognition of multiple substrates per transporter, and passive and active flux dependence on different ion equilibria, it is important to point out that a secretagogue effect may be indirect in the sense that an identified secretagogue compound may exert its effect through the shift of nominal ion balances and equilibria and thus altering the flux of the oxalate ion.

*O. formigenes* is a naturally occurring oxalate degrading bacterium, present in the GI-tracts of vertebrates, where it takes part in a complex symbiosis with the mammal host. Studies with *O. formigenes* support a promotion of enteric elimination of oxalate by inducing the trans epithelium flux of oxalate from a parenteral site to the intestinal lumen, when inhabiting the intestinal tract of rats and mice. Further, *O. formigenes* administration to human subjects with end-stage renal disease demonstrates a significant lowering of plasma oxalate (WO2005123116A2). These findings supported the inventors in their theorized concept of secreted compounds affecting the intestinal epithelia cell in a way favorable for *O. formigenes* survival in the intestinal tract of humans as well as rodents.

A large-scale process of manufacturing and using a potential secretagogue was explored, which led to the identification of protein compounds with a proposed secretagogue effect and the invention as described here. As many of the proteins are present at low amounts, the large-scale manufacturing process and subsequent purification and isolation made identification possible. To the best of our (present inventors) knowledge, there are currently no identified secretagogue compounds described for *O. formigenes* in the art and this is the first attempt of isolating and identifying them for use in hyperoxaluria therapy.

Based on investigations by the present inventors, compounds produced by *O. formigenes*, proposed to cause an induced secretory flux, have been manufactured at sufficient scale to be identified. The compounds (secretagogues) have been purified and characterized.

Thus, the present invention further provides a method of isolating a secretagogue in sufficient quantities for identification and proposed use in hyperoxaluria therapy. The isolation and enrichment of the secretagogue can be combined with the isolation of oxalate degrading bacteria; hence, resulting in one process pertaining to both harvest of oxalate degrading bacteria as well as an enrichment of compounds secreted by the oxalate degrading bacteria during fermentation.

The secretagogue compounds from *O. formigenes*, which should be produced in sufficient quantities for identification and use in hyperoxaluria therapy, are identified as one or more secretagogue proteins and peptides that individually or together exert a direct or indirect effect on oxalate flux in the intestinal tract of a mammal. The identified compounds are secreted out of the bacterial cell, or maintained intra-cellularly and released into culture media upon cell death. Cell death is a continuous process during cell culture growth; hence, proteins or other compounds, identified from cell-free culture media, with a proposed secretagogue effect, may not inherently be secreted compounds.

The secretagogue compounds may exert their combined or individual effects in the intestinal tract in a reaction necessitating a co-factor. Therefore, a combination of one or more co-factors (for example: NAD⁺, NADP⁺, FAD, CoA, ATP, ADP among others) and one or more secretagogues, if necessary to commence the secretagogue positive effect in the intestinal tract of a mammal, is also encompassed by this invention.

The secretagogue compounds may exert their combined or individual secretagogue effects indirectly by altering the nominal fluxes of other compounds for example, ions and small organic compounds and thereby cause a change in oxalate flux. Therefore, an indirect effect of the secretagogue compounds mentioned herein, which indirectly alters the oxalate flux through a change in flux of ions or small organic compounds, for example, is also encompassed by this invention.

The effect of the secretagogue compounds may be improved in combination with oxalate degrading bacteria, oxalate degrading enzyme(s), enzyme(s) involved in oxalate metabolism, cofactors, substrates, or combinations thereof.

Therefore, a combination of one or more oxalate degrading bacteria, oxalate degrading enzyme(s), enzyme(s) involved in oxalate metabolism, cofactors, substrates, and one or more secretagogues, if necessary to commence the secretagogue positive effect in the intestinal tract of a mammal, is also encompassed by this invention.

Disclosed herein is also a method of removing exogenous and/or endogenous oxalate through enteric elimination by administering the secretagogue itself, or together with oxalate degrading enzymes, oxalate degrading bacteria, enzyme(s) involved in oxalate metabolism, cofactor(s), substrate(s), to a mammal subject in need of oxalate removal.

The combined administration of one or more secretagogues and oxalate degrading bacteria, oxalate degrading enzyme(s), enzyme(s) involved in oxalate metabolism, cofactor(s), substrate(s), ensures both a stimuli of the oxalate flux, to increase oxalate transport in the direction of the intestinal lumen, as well as increased degradation of oxalate throughout the gastrointestinal tract.

Consequently, the present invention relates to pharmaceutical compositions comprising one or more identified components or secretagogues, derived from oxalate degrading bacteria, recombinantly expressed or extracted from conditioned media, administered to patients with or without one or more oxalate degrading bacteria, oxalate degrading enzymes, enzymes involved in oxalate metabolism, cofactors, substrates, or combinations thereof.

The pharmaceutical composition comprises an effective amount of a secretagogue. An effective amount of a secretagogue comprises an amount that will reduce a portion of the oxalate present systemically by secretion into the intestinal tract. The amount that can be used in a single dose composition, alone or in combination with oxalate-degrading bacteria and/or enzymes, can range from about 10 µg to 1000,000 µg, from about 100 µg to 100,000 µg, from about 1 mg to 100 mg, and all ranges encompassed therein.

This pharmaceutical composition may be resistant to degradation by gastric acid. The composition can be, for example, in the form of a tablet, capsule or bead, optionally provided with an enteric coating or other means for providing resistance to degradation in the stomach and the upper small intestine.

The invention further relates to a method of treating a subject in need, wherein the method comprises administering an effective amount of a secretagogue compound, derived from or produced by oxalate degrading bacteria, or a pharmaceutical composition comprising such a secretagogue compound administered with or without one or more oxalate degrading bacteria, oxalate degrading enzymes, enzymes involved in oxalate metabolism, cofactors, substrates, or combinations thereof, to thereby reduce the presence of oxalate in the subject. An effective amount of a secretagogue comprises an amount that will reduce a portion of the oxalate present systemically by secretion into the intestinal tract. The amount that can be used in a single dose composition, alone or in combination with oxalate-degrading bacteria and/or enzymes, can range from about 10 µg to 1000,000 µg, from about 100 µg to 100,000 µg, from about 1 mg to 100 mg, and all ranges encompassed therein.

Thus, the present disclosure provides a secretagogue (defined more in detail below) derived from oxalate degrading bacteria, e.g. from *Oxalobacter formigenes*, for use in the treatment of an oxalate related disease and/or oxalate related imbalance in a subject (defined more in detail below), wherein the administration of the secretagogue results in a reduction of urinary oxalate and/or plasma oxalate in the subject.

According to the present disclosure, the oxalate related disease may be selected from the group consisting of primary hyperoxaluria, hyperoxaluria, absorptive hyperoxaluria, enteric hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders/conditions caused by/associated with gastrointestinal surgery, bariatric surgery (surgery for obesity), and/or antibiotic treatment.

In accordance with the present disclosure, the secretagogue may comprise an amino acid sequence, which has a secretagogue activity and at least 85%, such as 90%, 95%, 96%, 97%, 98%, 99%, or 100% identity with an amino acid sequence according to any one of SEQ ID NO: 1-19.

The secretagogue may be recombinantly expressed in a suitable organism or extracted from conditioned media.

The present disclosure further provides a pharmaceutical composition comprising one or more secretagogues as defined above, optionally further comprising one or more oxalate degrading bacteria, oxalate degrading enzymes (defined more in detail below), enzymes involved in oxalate metabolism (defined more in detail below), cofactors (defined more in detail below), substrates (defined more in detail below), or combinations thereof.

The pharmaceutical composition may be formulated to have an enteral, parenteral or topical route of administration.

The present disclosure further provides a method for treating a subject suffering from an oxalate related disease, comprising administering to said subject a secretagogue derived from oxalate degrading bacteria, wherein administration of the secretagogue results in a reduction of urinary and/or plasma oxalate in the subject.

In said method, the secretagogue may comprise an amino acid sequence, which has a secretagogue activity and at least 85%, such as 90%, 95%, 96%, 97%, 98%, 99%, or 100% identity with an amino acid sequence according to any one of SEQ ID NO: 1-19.

The method may further comprise administering to said subject one or more oxalate degrading bacteria, oxalate degrading enzymes, enzymes involved in oxalate metabolism, cofactors, substrates, or combinations thereof.

In said method, the oxalate related disease is selected from the group consisting of primary hyperoxaluria, hyperoxaluria, absorptive hyperoxaluria, enteric hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders/conditions caused by/associated with gastrointestinal surgery, bariatric surgery (surgery for obesity), and/or antibiotic treatment.

The present disclosure also provides a method for preparing a secretagogue as defined above, comprising:

i) inoculating oxalate degrading bacteria, e.g. *Oxalobacter formigenes*, into a temperature equilibrated selective growth medium, specific for microbes utilizing oxalate as sole carbon source, said growth medium including oxalate as carbon source, necessary trace metals and amino acids under anaerobic conditions;

ii) transferring cell culture between containers under anaerobic conditions, such as between anaerobic bottles or between an anaerobic bottle and a fermenter, for example by using bottle ports and a sterile gas pressure to displace liquid through a non air-permeable tubing;

iii) harvesting a cell suspension, and processing of said cell suspension by using for example tangential flow filtration to separate whole cells and debris from the suspension, thereby obtaining a cell-free permeate;

iv) filtering the cell-free permeate to obtain a retentate, for example by using hollow fiber which selectively removes compounds of <10 k Da and peptides of reduced interest;

v) isolating one or more secretagogues from the retentate by using for example liquid chromatography, electrophoresis, precipitation, ultracentrifugation and/or concentrating spin columns.

Particularly, the present disclosure provides a secretagogue, derived from oxalate degrading bacteria, e.g. from *Oxalobacter formigenes*, for use in the treatment of an oxalate related disease and/or oxalate related imbalance in a subject, wherein the administration of the secretagogue results in a reduction of urinary oxalate and/or plasma oxalate in the subject, wherein the secretagogue compound comprises an amino acid sequence which has a secretagogue activity and at least 85%, such as 90%, 95%, 96%, 97%, 98%, 99%, or 100% identity, with an amino acid sequence according to any one of SEQ ID NO: 3, 4, 6, 13 and 19. Pharmaceutical compositions comprising such a secretagogue are also provided. Further, the present disclosure provides a method for treating a subject suffering from an oxalate related disease, comprising administering to said subject a secretagogue as defined above, as well as a method for preparing such a secretagogue.

BRIEF DESCRIPTION OF THE DRAWINGS

FIG. 1A: SEQ ID No. 3 expressed protein analysis.
FIG. 1B: SEQ ID No. 4 expressed protein analysis.
FIG. 1C: SEQ ID No. 6 expressed protein analysis.
FIG. 1D: SEQ ID No. 13 expressed protein analysis.
FIG. 1E: SEQ ID No. 19 expressed protein analysis.

DEFINITIONS

Figure 1:
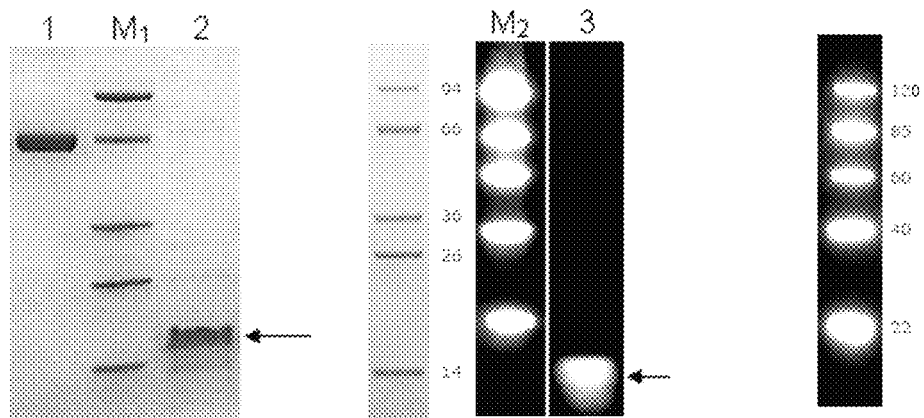
FIG. 1 A-E. SDS-PAGE Gels (left) and Western Blots (right) for recombinantly expressed *Oxalobacter formigenes* potential secretagogue proteins. Bovine Serum Albumin (2 ug) was run as control (Lane 1). Target protein on SDS-PAGE gel is presented in Lane 2, and target protein on Western blot is presented in Lane 3. Ladder weights are shown to the right of respective analysis image. M1=protein marker Genscript Cat. No. M00505. M2=protein marker Genscript Cat. No. MM0908.
Figure 1:
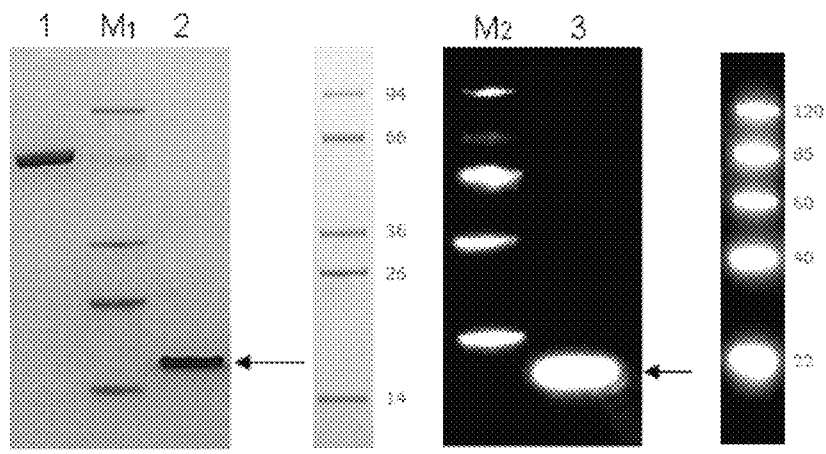
Figure 1:
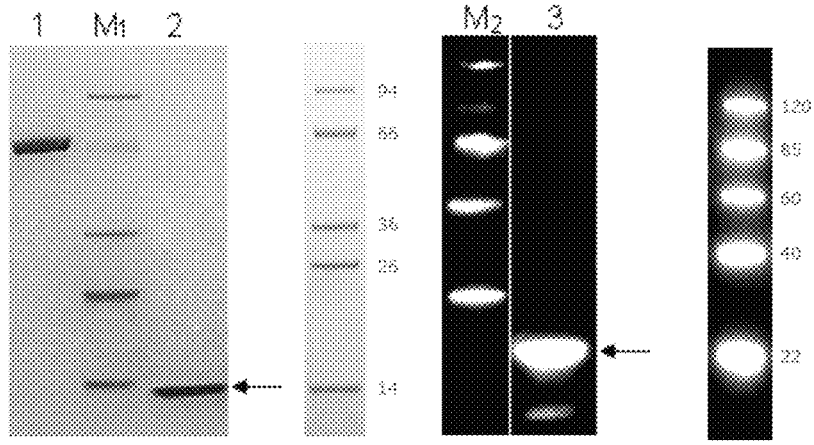
Figure 1:
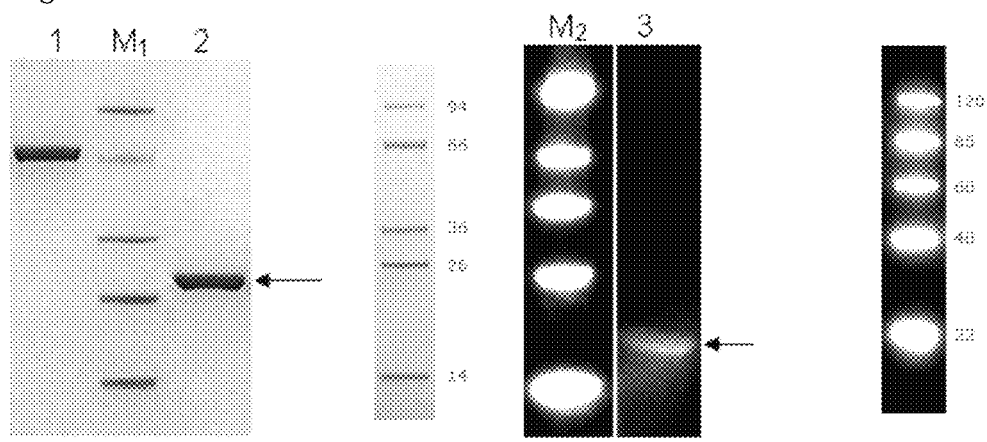
Figure 1:
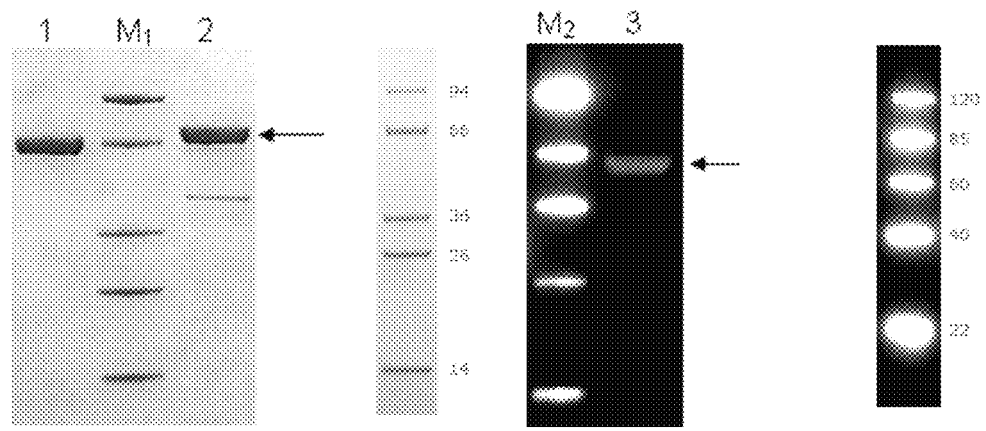

All terms used in the present text are intended to have the meaning usually given to them in the art. For the sake of clarity, some terms are also defined below.

Secretagogue

A secretagogue is a substance, component or compound that directly or indirectly promotes secretion of another substance, component or compound. Secretagogues can be peptides, hormones, proteins or small molecules. Herein the word secretagogue will be used for identified protein compounds, which have a proposed secretagogue effect in the body of a mammal.

The secretagogues described herein were isolated from the supernatant of an *O. formigenes* cell culture suspension and as such can originate from a secretion process or a cell death and lysis promoted release.

The secreted compounds and proposed secretagogues were characterised as proteins with a molecular weight ranging from 8.8-98.8 kDa, with >50% of compounds being in the span of 30-50 kDa. Of the nineteen proteins, thirteen were enzymes and the remaining six were proteins without known catalysing function. Of these six proteins, one was defined as "conserved hypothetical protein" i.e. this protein is found in organisms from several phylogenetic lineages but have not been functionally characterized. Another of the six proteins was defined as "predicted protein". This is used for entries without evidence at protein, transcript, or homology levels. The amino acid sequences of the identified proposed secretagogues are presented in Example 4, with sequence IDs: SEQ ID No: 1, SEQ ID No: 2, SEQ ID No:3, SEQ ID No:4, etc., to the last one, i.e. SEQ ID No: 19.

Five proteins, corresponding to amino acid sequence IDs: SEQ ID No: 3, 4, 6, 13 and 19, were recombinantly expressed in *E. coli* and screened for secretagogue activity of labeled oxalate over rat intestinal tissue in Ussing chambers. All recombinant proteins expressed demonstrated a reduced overall oxalate flux as compared to control. One protein in particular, of SEQ ID No. 3, had an effect that increased net secretion of labeled oxalate over rat distal intestinal tissue.

The secreted compounds are also described herein in terms of stability (Instability index II), thermostability (for globular proteins: aliphatic index) and solubility (GRAVY, Grand Average of Hydropathy), see Example 5. Three proteins were predicted as instable according to index (score >40): serine hydroxymethyltransferase, acyl carrier protein, riboflavin synthase subunit beta. In addition, the amino acid sequences of the secretagogues were investigated for potential signal peptide cleavage sites (see Example 6).

Conditioned Medium

A conditioned medium is a growth medium that has been used to grow a particular organism. The term conditioned refers to the fact that the organism has utilized components of the original medium composition for growth and metabolism, as well as released products of its metabolism and gene expression. A conditioned medium also contains and refers to products of metabolism and gene expression released upon the continuous cell death and lysis inherent to a culture growth. Conditioned media may also be referred to as cell-free culture suspensions. The conditioned medium described herein originates from an unconditioned medium with the composition described in Example 1. This unconditioned medium is a specialty medium developed specifically for the unique purpose of *O. formigenes* growth, and thus the concomitant secretagogue preparation as well, and contains oxalate as main source of carbon.

Oxalate-Degrading Enzyme

The term "oxalate-degrading enzyme" shall be construed as any enzyme that is capable of reducing oxalate, and includes oxalate decarboxylase, oxalate oxidase, formyl-CoA transferase and oxalyl-CoA decarboxylase. It may reduce oxalate per se and/or it may function in an oxalate reduction pathway. In this context the term "oxalate" encompasses oxalic acid and/or any salts thereof.

Enzyme Involved in Oxalate Metabolism

The term "enzyme involved in oxalate metabolism" shall be construed as any enzyme functioning in a pathway relating to oxalate metabolism, and includes alanine-glyoxylate aminotransferase (AGT), glyoxylate reductase (GR) and 4-hydroxy-2-oxoglutarate aldolase (HOGA).

Co-Factor

The term "co-factor" shall be construed as a non-enzymatic compound necessary for the activity of an enzyme, and includes vitamin $B_6$, $NAD^+$, $NADP^+$, FAD, CoA, ATP and ADP.

Substrate

The term "substrate" shall be construed as the ingoing compound of an enzyme catalyzed reaction, and includes oxalate, glyoxylate, and 4-hydroxy-2-oxoglutarate, among others.

Oxalate-Related Disease and/or Oxalate Related Imbalance

The term "oxalate-related disease and/or oxalate related imbalance" shall be construed as diseases that are caused or realized by an imbalance in systemic oxalate levels, and includes primary hyperoxaluria, hyperoxaluria, absorptive hyperoxaluria, enteric hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders/conditions caused by/associated with gastrointestinal surgery, bariatric surgery (surgery for obesity), and/or antibiotic treatment.

DETAILED DISCLOSURE OF THE INVENTION

The invention described herein relates to one or more protein secretagogues identified from a cell-free culture suspension originating from an *O. formigenes* culture. The identified protein secretagogues exert an effect on the oxalate transport in the intestinal tract of an animal or human. The proposed effect, described above, exerted by the identified protein secretagogues is a result of an impact from one identified protein secretagogue or from a combination of two identified secretagogues, three identified secretagogues, four identified secretagogues, five identified secretagogues or six or more identified secretagogues. The identified compounds may exert a positive effect in the intestine of animals or humans, which will positively influence critical conditions as described herein, when administered as described herein.

The effect exerted in the intestinal tract of an animal or human by the action of one or more *O. formigenes* derived secretagogues may require a co-factor of sorts. Therefore, a potential co-factor, which ensures a positive effect on oxalate flux in the intestine in combination with one or more secretagogues, should also be considered encompassed by this invention. The co-factor which may be necessary for the secretagogue to exert a positive action within the intestinal tract of an animal or human, as described above, includes but is not limited to: $NAD^+$, $NADP^+$, FAD, CoA, ATP, ADP.

The effect exerted in the intestinal tract of an animal or human by the action of one or more *O. formigenes* derived secretagogues may be improved with the inclusion of one or more oxalate degrading bacteria, oxalate degrading enzyme(s), enzyme(s) involved in oxalate metabolism, cofactors, substrates, or combinations thereof. Therefore, one or more oxalate degrading bacteria, oxalate degrading enzyme(s), enzyme(s) involved in oxalate metabolism, cofactor(s), substrate(s), or combinations thereof, which ensures a positive effect on oxalate flux in the intestine in combination with one or more secretagogues, should also be considered encompassed by this invention.

The oxalate degrading bacterium that may improve the effect of the secretagogue(s) is preferably *O. formigenes*.

The oxalate-degrading enzyme(s) that may improve the overall effect in combination with one or more secretagogues include but is not limited to oxalate decarboxylase, oxalate oxidase, formyl-CoA transferase and oxalyl-CoA decarboxylase.

The enzyme(s) involved in oxalate metabolism that may improve the overall effect in combination with one or more secretagogues include but are not limited to alanine-glyoxylate aminotransferase (AGT), glyoxylate reductase (GR) and 4-hydroxy-2-oxoglutarate aldolase (HOGA).

The co-factors that are referred to above include but are not limited to vitamin $B_6$, $NAD^+$, $NADP^+$, FAD, CoA, ATP and ADP. Substrates referred to in the pharmaceutical composition include but is not limited to oxalate, glyoxylate, 4-hydroxy-2-oxoglutarate, among others.

The secretagogue compounds may exert their combined or individual secretagogue effects indirectly by altering the nominal fluxes of other compounds for example, ions and small organic compounds and thereby cause a change in oxalate flux. For example, it is known in the field that the transporters with oxalate affinity also demonstrate affinity for other small compounds or ions. For sake of description and without limiting the scope of this invention, those ions and small compounds include but are not limited to; carbonate, sulphate, chloride, sodium and formate to mention a few. Therefore, by altering the balances of these ions and small compounds, the flux of oxalate could be altered. Thus, an indirect effect of the secretagogue compounds mentioned herein, that indirectly alters the oxalate flux through a change in flux of ions or small organic compounds, for example, is also encompassed by this invention.

The identified protein secretagogue that exerts a direct or indirect effect, individually or in combination with other identified secretagogue(s), oxalate degrading bacteria, enzyme(s), co-factor(s), and/or substrates, on the oxalate transport in the intestinal tract of animals or humans includes: tartronic semialdehyde reductase, cysteine synthase A, acyl carrier protein, predicted protein (accession number: gi|237749499), methionine adenosyltransferase 1, YgiW protein, riboflavin synthase subunit beta, alkyl hydroperoxide reductase/thiol specific antioxidant/mal allergen, phospho-2-dehydro-3-deoxyheptonate aldolase, elongation factor Tu, s-adenosylhomocysteine hydrolase, conserved hypothetical protein (accession number: gi|237747886), diaminopimelate dehydrogenase, serine hydroxymethyltransferase, aspartate-semialdehyde dehydrogenase, malic enzyme, aconitate hydratase 1, hsp70-like protein. The secretagogue according to the present invention is a polypeptide comprising an amino acid sequence, which has a secretagogue activity and at least 85% identity, such as 90%, 95%, 96%, 97%, 98%, 99%, or 100% identity, with an amino acid sequence according to any one of SEQ ID NO: 1-19.

Without limiting the scope of this invention, it is noted that after analysis of the amino acid sequence, the YgiW protein (accession number: gi|237748090) was predicted to have a signal peptide cleavage site between amino acid number 28 and 29 (ASA-QY). A signal peptide on a protein has the purpose of targeting the protein to a particular location inside (a certain organell) or outside of the cell. Secreted proteins and membrane proteins are also localized using signal peptides.

In addition, without affecting the scope of this invention, it has been noted that the calculated pI of one of the proteins identified (YgiW: accession number: gi|237748090) was as high as 9.33. This pI means that the protein has a net positive charge at physiological pH. It is well known that most bio surfaces carry a net negative charge; hence, a high net positive charge of a protein supports a function, which is interactive with either a bio surface or a bio membrane. It is likely that anything supporting interaction of a potential secretagogue compound with a bio surface facilitates the process of promoting secretion by the same.

The proposed effect exerted by the identified protein secretagogues, individually or in combination with other identified secretagogue(s), bacteria, enzyme(s) co-factor(s), and/or substrates, on the oxalate transport in the intestinal tract of animals or humans, includes but is not limited to: a direct or indirect interaction with a membrane protein or membrane transporter, an indirect interaction with an expression factor within the epithelial cells or the genome of the epithelial cells. The membrane transporters referred to above may include but are not limited to SLC26A1 (SAT1), SCL26A2 (DTDST), SLC26A3 (DRA), SLC26A6 (PAT1 or CFEX), SLC26A7, and SCL26A9. In addition, the interaction may be any modulation i.e. any activity including but not limited to: increase, enhance, agonize, promote, decrease, reduce, suppress, block, or antagonize.

Method of Isolation

The present invention provides a method of producing secretagogues. The invention further provides a method of isolating the secretagogues with a low product loss. The production of the secretagogues involves a seed train using vials, anaerobic bottles or fermenters in any combination, in one, two, three, four or more steps. The medium composition, growth conditions, fermentation time, harvest and filtration steps used are all described in Examples 1 and 2 and are covered under this present invention for the production of secretagogues. Any other addition, subtraction or general alteration as reasonable for anyone skilled in the art also falls under this invention.

The fermentation process for producing a secretagogue may involve modifications to induce the secretagogue production by *O. formigenes* cells by using different means of induction, for example, varied or lower concentrations of oxalate, varied exposure to or concentration of formate, and/or other forms of stress induction. Such an induction modification to the process, or other means of induction to promote secretion of an active secretagogue, as reasonable to those skilled in the art, are considered to be encompassed by this invention.

The isolation of secretagogues preferably uses Tangential Flow Filtration (TFF) and hollow fiber filtration steps but may include other commonly used methods of isolation of proteinaceous species as reasonable for those skilled in the art.

The isolation and enrichment of the secretagogue may be combined with the isolation of oxalate degrading bacteria; hence, resulting in one process pertaining to both harvest of oxalate degrading bacteria as well as an enrichment of compounds secreted by the oxalate degrading bacteria during fermentation. This process includes but is not limited to methods such as centrifugation, TFF, hollow fiber and other methods of cell collection, filtration and concentration as reasonable for those skilled in the art.

The identified secretagogue may also be expressed recombinantly. The recombinantly expressed proteins may originate from a naturally extracted or synthesized gene sequence having at least 85% sequence identity to the sequences of SEQ ID No:s 1-19. Protein homologs and variants include but are not limited to: polymorphic variants and natural or artificial mutants, modified polypeptides in which one or more residue is modified, and mutants comprising one or more modified residues. Mutations include but are not limited to truncation, deletion, substitution or addition mutations of nucleic acids.

The recombinant enzymes may be expressed in a wide variety of hosts, known to those skilled in the art of protein expression, including but not limited to: *E. coli, Lactobacillus* spp, *Bacillus* spp etc.

For a recombinant production of the enzyme or protein the host should comprise a construct in the form of a plasmid, vector, phagemid, or transcription or expression cassette that comprises the enzyme or protein or a functional fragment thereof. A variety of constructs are available, including constructs, which are maintained in single copy or multiple copy. Many recombinant expression systems, components, and reagents for recombinant expression are commercially available, for example from Invitrogen Corporation (Carlsbad, Calif.); U.S. Biological (Swampscott, Mass.); BD Biosciences Pharmingen (San Diego, Calif.): Novagen (Madison, Wis.); Stratagene (La Jolla, Calif.); and Deutsche Sammlung von Mikroorganismen and Zellkulturen GmbH (DSMZ), (Braunschweigh, Germany).

A heterologous promotor, including a constitutive and/or inducible promotor, optionally controls recombinant expression of the proteins. Promotors such as, for example, T7 or other promotors, as suitable for the host, and which are well-known for those skilled in the art. The promotor may also originate from the *Oxalobacter* genus.

The enzyme's or protein's recombinant nucleic acid sequence may include nucleic acids for purposes additional to the expression of the protein, including but not limited to for purification purposes, folding purposes etc. Examples of those are: secretion sequences, signal sequences, linkers, expression control elements, affinity tags, to name a few. The amino acids resulting from these nucleic acid sequences may or may not be removed after expression of the protein. All the constructs mentioned above may be used for expression of the enzymes and proteins, which will be used in methods described herein.

The host cells will be transformed/transfected with the chosen expression system, outlined above. The cells will be cultured using methods known to those skilled in the art, this include liquid cultures in shake flasks and fermenters as well as solid cultures in plates etc.

The proteins may be purified from the source, such as a natural or recombinant source, prior to being used in methods outlined herein. Purification may comprise extraction from the host cells by means of sonication, French press, glass beads or other mean of physical lysis, or chemical cell lysis, and separation by chromatographic steps or other means as known to those skilled in the art. Optionally, a concentration step may be used, e.g., by dialysis, chromatofocusing chromatography, and/or associated with buffer exchange.

Compounds and Compositions

The compounds and compositions of the present invention are suitable for use in reducing oxalate levels in humans or animals.

An identified protein species, with a secretagogue effect, and an oxalate-degrading particle or cell and/or necessary co-factor(s), in a composition of the current invention is administered in an effective amount to an individual. An effective amount comprises an amount of one or several components or secretagogues, derived from or produced by oxalate degrading bacteria, together with one or more oxalate degrading enzymes or bacteria. The effective amount is sufficient, optionally in combination with oxalate-degrading activity from bacteria or enzyme(s), to reduce systemic oxalate for a clinical effect in a disease state. The amount that can be used in a single dose composition, alone or in combination with oxalate-degrading bacteria and/or enzymes, can range from about 10 μg to 1000,000 μg, from about 100 μg to 100,000 μg, from about 1 mg to 100 mg, and all ranges encompassed therein. The component or secretagogue will actively promote flux of oxalate to the intestine, where one or more oxalate degrading enzymes or bacteria will degrade the oxalate.

The present invention also relates to pharmaceutical compositions comprising one or more identified components or secretagogues, derived from oxalate degrading bacteria, recombinantly expressed or extracted from conditioned media, which pharmaceutical compositions may be administered with or without oxalate degrading enzyme(s), enzyme(s) involved in oxalate metabolism, cofactor(s), oxalate degrading bacteria and/or substrate(s). In a preferred embodiment, this pharmaceutical composition is resistant to degradation by gastrointestinal acids and degrading enzymes in the stomach and the upper small intestine. The composition can be, for example, in the form of a tablet or capsule.

The oxalate degrading bacteria that may be administered in combination with (i.e. that may additionally be present in a composition comprising) one or more identified compounds or secretagogues are O. formigenes.

The oxalate-degrading enzyme administered in combination with (i.e. that may additionally be present in a composition comprising) one or several identified secretagogues include but is not limited to oxalate decarboxylase, oxalate oxidase, formyl-CoA transferase and oxalyl-CoA decarboxylase.

The enzyme(s) administered in combination with (i.e. that may additionally be present in a composition comprising) one or several identified secretagogues include but are not limited to alanine-glyoxylate aminotransferase (AGT), glyoxylate reductase (GR) and 4-hydroxy-2-oxoglutarate aldolase (HOGA).

The co-factors administered in combination with (i.e. that may additionally be present in a composition comprising) one or several identified secretagogues include but are not limited to vitamin $B_6$, $NAD^+$, $NADP^+$, FAD, CoA, ATP and ADP. Substrates referred to in the pharmaceutical composition include but is not limited to oxalate, glyoxylate, 4-hydroxy-2-oxoglutarate, among others.

The oxalate degrading enzyme(s), enzyme(s) involved in oxalate metabolism, cofactor(s), bacteria and/or substrate(s) administered in combination with one or several identified secretagogues may be administered in the same or different fashion in accordance with the most suitable method for optimal bioavailability and activity, as known in the art. The administration methods related include but are not limited to enteral, parenteral and/or topical.

The combined administration of one or more secretagogues and O. formigenes, oxalate degrading enzyme(s), enzyme(s) involved in oxalate metabolism, cofactor(s), and/or substrate(s), ensures both a stimuli of the oxalate flux, to increase oxalate transport in the direction of the intestinal lumen, as well as increased degradation of oxalate throughout the gastrointestinal tract.

Use of Particles and Compositions—Method for Treatment

Methods of the present invention comprise providing a composition according to the invention comprising one or several identified secretagogues produced by oxalate degrading bacteria administered with or without oxalate degrading enzyme(s), enzyme(s) involved in oxalate metabolism, cofactor(s), oxalate degrading bacteria and/or substrate(s). The identified components or secretagogues of this composition include, but are not limited to; tartronic semialdehyde reductase, cysteine synthase A, acyl carrier protein, predicted protein (accession number: gi|237749499), methionine adenosyltransferase 1, YgiW protein, riboflavin synthase subunit beta, alkyl hydroperoxide reductase/thiol specific antioxidant/mal allergen, phospho-2-dehydro-3-deoxyheptonate aldolase, elongation factor Tu, s-adenosylhomocysteine hydrolase, conserved hypothetical protein (accession number: gi|237747886), diaminopimelate dehydrogenase, serine hydroxymethyltransferase, aspartate-semialdehyde dehydrogenase, malic enzyme, aconitate hydratase 1, hsp70-like protein, and comprise a sequence having at least 85% sequence identity, such as 90%, or 95%, sequence identity, to the sequences outlined in Example 4, with sequence IDs: SEQ ID No: 1, SEQ ID No: 2, SEQ ID No:3, SEQ ID No:4, etc., to the last one, i.e. SEQ ID No: 19.

The compositions of the present invention are suitable in methods of reducing oxalate levels in the animal or human body and are used in the treatment or prevention of oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders/conditions caused by/associated with gastrointestinal surgery, bariatric surgery (surgery for obesity), and/or antibiotic treatment.

Methods of the present invention comprise administering a composition that enables increased net flux of oxalate from plasma to the intestine for degradation by one or more oxalate degrading enzymes or bacteria. A method of providing one or several identified components or secretagogues produced from one or more oxalate degrading bacteria, or derived from oxalate degrading bacteria and recombinantly expressed, to the stomach and/or small intestines by providing a formulation according to the invention.

A reduction in oxalate may be achieved by providing one or several identified components or secretagogues with oxalate degrading enzyme(s), enzyme(s) involved in oxalate metabolism, cofactor(s), bacteria and/or substrate(s) to the gastrointestinal tract. The compositions of the present invention are useful in degrading the oxalate secreted into the intestine from the circulatory system, and thus the methods of the present invention contemplate an overall reduction of the oxalate load in an individual.

The reduction may be measured in any tissue or body fluid environment of the subject. Body fluids include secretions of the body such as nasal or gastric secretions, saliva, blood, serum, plasma, urine, chyme or digestive matter, tissue fluid, and other fluid or semi-solid materials made by humans or animals. For example, oxalate reducing enzyme particle compositions and/or bacteria can be administered to a human or animal to induce a net flux of oxalate to the intestines where the oxalate-reducing enzyme activity degrades the oxalate present in the subject.

Methods for reducing oxalate levels in a human or animal and treating and preventing oxalate-related conditions comprise administering one or several identified components or secretagogues derived from one or more oxalate degrading bacteria, recombinantly expressed or extracted from conditioned media, together with or without one or more oxalate degrading enzyme(s), enzyme(s) involved in oxalate metabolism, cofactor(s), bacteria and/or substrate(s). An effective amount comprises an amount of one or several components or secretagogues, derived from or produced from one or more oxalate degrading bacteria, together with or without one or more oxalate degrading enzymes and/or bacteria and/or co-factor(s) that will reduce the oxalate present in the intestines, tissues or bodily fluids of the subject or maintain a lowered amount of oxalate in the subject compared to the amount of oxalate present before administration of the composition. Such an effective amount can range from about 10 µg to 1000,000 µg, such as from about 100 µg to 100,000 µg, or from about 1 mg to 100 mg, of the secretagogue, alone or in combination with oxalate-degrading bacteria and enzymes.

In a treatment method, an effective amount of a composition/compound/secretagogue is administered orally to be ingested by a subject at least once a day, at least twice a day, at least three times a day, at least four times a day or more if necessary, and such administration can last for one day, two days, three days, four days, five days, or a week, two weeks, three weeks, or a month, two months, three months, four months, five months, six months, more than six months, one year, two years, or for years or continuously throughout the life of the patient. Such treatment may be continued to maintain the desired oxalate levels in a subject.

All patents, patent applications and references included herein are specifically incorporated by reference in their entireties.

It should be understood, of course, that the foregoing relates only to exemplary examples of the present invention and that numerous modifications or alterations may be made therein without departing from the spirit and the scope of the invention as set forth in this disclosure.

Although the exemplary examples of the present invention are provided herein, the present invention is not limited there. There are numerous modifications or alterations that may suggest themselves to those skilled in the art.

The present invention is further illustrated by way of the examples contained herein, which are provided for clarity of understanding. The examples should not to be construed in any way as imposing limitations upon the scope thereof. On the contrary, it is to be clearly understood that changes can be made to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Proposed Secretagogues of *O. formigenes*.

To prepare sufficient amounts for identification, the proposed secretagogues were isolated from a 400 L fermentation. This culture suspension was produced in a four-step seed train (500 mL to 400 L) inoculated from a glycerol master cell bank. All steps of the seed train used sterile anaerobic specialized oxalate media (100 mM oxalate) composed of trace metals and the following compounds in gm/L: 0.25 potassium phosphate monohydrate, 0.25 potassium phosphate dihydrate, 0.5 ammonium sulfate, 0.025 magnesium sulfate, 0.02 EDTA (disodium salt), 1.36 sodium acetate trihydrate, 0.001 resazurin sodium salt, 1 yeast extract, 13.4 sodium oxalate, 4 sodium carbonate (anhydrous), 0.5 L-Cystein HCl. The fermenter media (40 L and 320 L) was prepared without resazurin. All transfers during the fermentation process were performed when the seed had reached late log phase growth. The fermentation progressed as follows: an anaerobic bottle containing 500 ml of oxalate media (37° C.) was inoculated with 1% *O. formigenes* MCB and grown at 37° C., 75 rpm until reaching late exponential phase. Subsequently the culture was anaerobically transferred, using sterile syringes, needles and $CO_2$ gas, into an anaerobic bottle containing 3.5 L of oxalate media and incubated at 37° C., 75 rpm until reaching late exponential phase. The grown seed culture (total volume 4 L) was inoculated into a 100 L seed fermenter containing 40 L of sterile anaerobic specialized oxalate media. The seed fermenter culture was transferred to a 500 L fermenter containing 320 L oxalate media after reaching late exponential phase. Harvest of the total 400 L of culture suspension was performed when the culture had reached late exponential phase.

Example 2

Isolation of Proposed Secretagogues from 400 L Culture Suspension.

Harvest of the cells from the final culture suspension was performed using Tangential Flow Filtration (TFF) with a 500 kDa nominal molecular weight cut-off filter. The resulting cell-free filtrate was further processed through a 10 kDa hollow fiber. The retentate was aseptically collected and intermittently stored at 4° C. before being sterile filtered using 0.2 µm bottle top filters into 250 mL aliquots. The bottles were subsequently frozen for long-term storage at −80° C. In a subsequent step, the retentate was further processed using concentrator centrifuge tubes with a nominal molecular weight cut-off of 3 kDa for an additional concentration of approximately 90-fold. Protein concentration was determined on the final concentrate using Bradford assay and Coomassie reagent. Bovine Serum Albumin (BSA) was used for standard curve preparation. The final concentrate was a clear yellow liquid with 1 mg of total protein per mL.

Example 3

Identification of Proposed Secretagogues Using LC-MS/MS.

Sample Preparation (Trypsin Digest)

The protein concentrate was re-dissolved 100 µL 50 mM NH4HCO3 under agitation and 5 µL 200 mM DTT was added. Sample was heated to 95° C. for 5 minutes. Protein was alkylated by adding 4 µL 1M iodoacetamide in 100 mM $NH_4HCO_3$ and let to react (45 min, 25° C., dark). Alkylation was stopped by adding 20 µL of 200 mM DTT and incubating (25° C., 45 min). Trypsin in $NH_4HCO_3$ was added to the sample in a ratio of trypsin to protein 1:50 and incubated (37° C., 16-18 h).

LC-MS/MS Analysis

The enzymatically digested samples were injected onto a capillary trap and desalted (3 µl/min 0.1% v/v formic acid for 5 min). Samples were then loaded onto a nanoflow HPLC column with elution gradient (Solvent A 97-60 Solvent B 3-40%) over 95 min with a 25 min re-equilibration for protein identification. Solvent A consisted of 0.1% v/v formic acid, 3% v/v ACN, and 96.9% v/v H2O.

Solvent B consisted of 0.1% v/v formic acid, 96.9% v/v ACN, and 3% v/v H2O. LC-MS/MS analysis was carried out on a hybrid quadrupole-TOF mass spectrometer using 225 V focusing potential and 2400 V ion spray voltage. Information-dependent acquisition (IDA) mode of operation was employed with a survey scan (m/z 400-1800) followed by collision-induced dissociation (CID) of the four most intense ions. Survey and MS/MS spectra for each IDA cycle were accumulated for 1 and 3 s, respectively.

Protein Search Algorithm

Tandem mass spectra were extracted by ABI Analyst version 2.0. All samples were analyzed using Mascot (Matrix Science, London, UK; version 2.2.2) set up to search NCBI (taxonomy bacteria database assuming digestion enzyme trypsin). Mascot was searched with 0.50 Da fragment ion mass tolerance and 0.50 Da parent ion tolerance. Iodoacetamide derivative of Cys, deamidation of Asn and Gln, oxidation of Met, was specified in Mascot as variable modifications. Scaffold (version Scaffold-3.3.2, Proteome Software Inc., Portland, Oreg.) was used to validate MS/MS based peptide and protein identifications. Peptide identifications are accepted if they could be established at greater than 95.0% probability as specified by the Peptide Prophet algorithm (Keller, A., et al., Anal Chem 74, 5383-92 (2002)). Protein identifications are accepted if they can be established at greater than 99.0% probability and contain at least 2 identified unique peptides. Protein probabilities were assigned by the Protein Prophet algorithm (Nesvizhskii, A. I., et al., Anal Chem 75, 4646-58 (2003)).

Results

The secreted compounds were characterised as proteins with a molecular weight ranging from 8.8-98.8 kDa, with >50% of compounds being in the span of 30-50 kDa. Table 1 below lists the proteins identified and the sequence origin (human strain *O. formigenes* OXCC13). *O. formigenes* OXCC13 is of the same sub-grouping (group 1) as *O. formigenes* HC-1; its complete genome has been sequenced and is thus searchable.

Of the nineteen proteins, thirteen were enzymes with a known catalysing function and the remaining six were proteins. Of the six proteins, one was defined as "conserved hypothetical protein" i.e. this protein is found in organisms from several phylogenetic lineages but have not been functionally characterized. Another of the six proteins was defined as "predicted protein". This is used for entries without evidence at protein, transcript, or homology levels.

Example 4

Amino Acid Sequences of Proteins Identified from *O. formigenes* OXCC13.

The 19 amino acid sequences presented herein (SEQ ID NO:s 1-19) are the results from the protein identification described in Example 3 and the respective identification numbers (gi number and RefSeq accession number (zp). The sequences are searchable using any of these identifying numbers.

```
tartronic semialdehyde reductase [Oxalobacter
formigenes OXCC13] gi|237749254|ref|
ZP_04579734.1|
                                          SEQ ID NO: 1
MANLGFIGLGIMGVPMAVNLQNGGNKLFVNDKKAPPAALTDGGAKACATG

AEVAKNADIIFIMVPDTPDVEAVLFGENGVAQGLSAGKIVVDMSSISPIA

TKEFAKKINDLGCEYLDAPVSGGEVGAKAGSLTIMVGGKEETFNKVKPLF

ELMGKNITLVGGNGDGQTTKVANQIIVALNIQAVAEALLFASKAGADPAK

VRQALMGGFASSRILEVHGERMINRTFNPGFRINLHQKDLNLALQGAKAL

GISLPNTATAQELMNACAANGLSGMDHSALCRAVEIMSAHEIAKA cysteine synthase A [Oxalobacter formigenes
OXCC13] gi|237748046|ref|ZP_04578526.1|
                                          SEQ ID NO: 2
MSNIAKSATDLIGNTPLLEISRFGKHVDADATILAKLEYFNPAGSAKDRI

AKAMIDAAEADGKLIPGSTI

IEPTSGNTGIALAAVGAARGYRVIITMPETMSVERQKLIRGYGADLVLTE

GAKGMKGAIEKAQELAATIPGGFVPLQFANPANPAIHKATTGPEIWRDTD

GKVDIFVAGVGTGGTLTGVGKYLKEQNPAVQVVAIEPAASPVLAGGKPGP

HKIQGIGAGFIPEALDVNVFDEVIGVPNDAAFATAKTLAHAEGVLVGISS

GAALWAASELAKRPENRGKTIVVLLADNGERYLSTDLFSN acyl carrier protein [Oxalobacter formigenes
OXCC13] gi|237747699|ref|ZP_04578179.1|
                                          SEQ ID NO: 3
MSDIEQRVKKIVAEQLGVAEDEIKLESSFVDDLGADSLDTVELVMALEDE

FEIEIPDEQAEKITTVQQAVDYATANMQS predicted protein [Oxalobacter formigenes OXCC13]
gi|237749499|refI|ZP_04579979.1|
                                          SEQ ID NO: 4
MKLRPLQDRIIVKRVDQEKTTASGIVIPDNAAEKPDQGEVIAVGNGKVLE

DGKVLPLDVKVGDIVLFGKYSGQTVKVEGEELLVMHESDVMAIVQN methionine adenosyltransferase 1 [Oxalobacter
formigenes OXCC13] gi|237747590|ref|ZP_04578070.1|
                                          SEQ ID NO: 5
MSQDYLFTSESVSEGHPDKVADQISDAILDAILEQDPHARVAAETLCNTG

LVVLAGEITTTANIDYISVA

RDTIKRIGYDNNDYGIDHRGCAVLVGYDKQSPDIAQGVDEGRGIDLDQGA

GDQGLMFGYACDETPELMPAAIYYAHRLVERQSQLRKDGRIAWLRPDAKS

QVTLRYVDGKPVAAETIVLSTQHAPEVEHKQIEEAVIEEIIKPVMPAEWL

KESKYLVNPTGRFVIGGPQGDCGLTGRKIIVDTYGGSCPHGGGAFSGKDP

SKVDRSAAYAARYVAKNIVAAGLAKKCQIQVSYAIGVARPINITINTEGT

GVIADSKIAALVNDHFDLRPKGIVQMLDLLHPRYVKTAAYGHFGRDEPEF

TWEKTDKAADLRQAAGL

YgiW protein [Oxalobacter formigenes OXCC13]
gi|237748090|ref|ZP_04578570.1|
                                          SEQ ID NO: 6
MMSKKLLTGLFAAGLSIGMLAVSSTASAQYIGPTRIAPTTVNKVLKSPVD

DQYVLLSGKITSQVSKDKYTFTDKTGSIVVEIDNEVFAGRQVGPDTQVEI

WGKVDKDMFKEPKIDVKRLGIPNQTK riboflavin synthase subunit beta [Oxalobacter
formigenes OXCC13] gi|237749243|ref|ZP_04579723.1|
                                          SEQ ID NO: 7
MMTVNTFEIDLQGQDLRIGIVQSRFNEEICRGLLGACLEELKRLGVADED

ILVATVPGALEIPTALQKMAESQQFDALIAVGGIIKGETYHFELVSNESA

AGISRVALDFDMPIANAILTTYTDEQAEARMVEKGTEAARVAVEMANLVM

AIDELEPPEEDE
``` alkyl hydroperoxide reductase/Thiol specific
antioxidant/Mal allergen [Oxalobacter formigenes
OXCC13] gi|237747586|ref|ZP_04578066.1|
SEQ ID NO: 8
MSSLINTEIIPFKAQAYHNGQFVKVTDADLKGKWSVVFFYPADFSFVCPT
ELGDLADHYEEFKKLGVEIYSVSTDTHFVHKGWHDASDTIKKIQFPMVGD
PSGQISRNFNVLIDDDGVALRGTFVINPEGVIKLCEIHDLGIGRSATELL
RKVQAAQYVATHKGQVCPASWQPGAETLAPSLDLVGKI Chain A, Formyl-Coa Transferase With Aspartyl-Coa
Thioester Intermediate Derived From Oxalyl-Coa
gi|163931105|pdb|2VJK|A
SEQ ID NO: 9
MTKPLDGINVLDFTHVQAGPACTQMMGFLGANVIKIERRGSGDMTRGWLQ
DKPNVDSLYFTMFNCNKRSIELDMKTPEGKELLEQMIKKADVMVENFGPG
ALDRMGFTWEYIQELNPRVILASVKGYAEGHANEHLKVYENVAQCSGGAA
ATTGANDGPPTVSGAALGDSNSGMHLMIGILAALEIRHKTGRGQKVAVAM
QDAVLNLVRIKLRDQQRLERTGILAEYPQAQPNFAFDRDGNPLSFDNITS
VPRGGNAGGGGQPGWMLKCKGWETDADSYVYFTIAANMWPQICDMIDKPE
WKDDPAYNTFEGRVDKLMDIFSFIETKFKADKDKFEVTEWAAQYGIPCGPV
MSMKELAHDPSLQKVGTVVEVVDEIRGNHLTVGAPFKFSGFQPEITRAPL
LGEHTDEVLKELGLDDAKIKELHAKQVV phospho-2-dehydro-3-deoxyheptonate aldolase
[Oxalobacter formigenes OXCC13] gi|237749194|
ref|ZP_04579674.1|
SEQ ID NO: 10
MDTTDDLRILAMKELTPPAHLIREFPCEEKAAETVSGCRKAIQRVLHNQD
DRLVVIIGPCSIHDPKAAMEYAHRLAEEKERYGDELVVVMRVYFEKPRTT
IGWKGLINDPFMDHSYRINEGLHIARELLRDVNELGLPAATEYLDMISPQ
YVADMISWGAIGARTTESQVHRELSSGLSCPVGFKNGTDGNIKIAIDAIK
AASHPHHFLSVTKGGHTAIFETEGNQDCHIILRGGYKPNYDAASVNEAAR
AVEAAGLAPKIMIDASHGNSSKKAENQVPVSLEVGENIAKGDDRIIGLMI
ESNLVGGRQDHEVGKKLVYGQSVTDACIGWEDSSKLLGQLAETVKRRRDV
LKK elongation factor Tu [Oxalobacter formigenes
OXCC13] gi|237747517|ref|ZP_04577997.1|
SEQ ID NO: 11
MSKKFGGEAKDYDQIDAAPEEKARGITINTSHVEYETAARHYAHVDCPGH
ADYIKNMITGAAQMDGAILVVSAADGPMPQTREHILLARQVGVPYIIVFL
NKCDMVDDAELLELVEMEVRELLSRYEFPGDDIPIIKGSAKLALEGDAGE
LGETAILALADALDSYIPTPERAVDGAFLMPVEDVFSISGRGTVVTGRVE
RGIIKVGEEIEIVGIKETAKTTCTGVEMFRKLLDQGQAGDNIGVLLRGTK
REEVERGQVLAKPGSIKPHLNFEGEVYVLSKEEGGRHTPFFNNYRPQFYF
RTTDVTGAIELPKDKEMVMPGDNVSISVKLISPIAMEEGLRFAIREGGRT
VGAGVVAKITE S-adenosylhomocysteine hydrolase [Oxalobacter
formigenes OXCC13] gi|237749247|ref|ZP_04579727.1|
SEQ ID NO: 12
MNAVSKTEQDFYIADPDLTAWGNKEIRIAETEMPGLMAIREEYAASKPLS
GARISGSLHMTIQTAVLIQTLEALGAKVRWASCNIYSTQDHAAAAIASNG
TPVFAFKGESLDDYWEFTHRIFEWPDGGYSNMILDDGGDATLLLHLGSRA EKDATVLDNPGSEEEVCLFNAIKRHLKTDPNWYSKRIKEIKGVTEETTTG
VHRLYQMHEEGKCLKFPAINVNDSVTKSKFDNLYGCRESLVDGIKRATDV
MIAGKVAVVGYGDVGKGCAQALKALSAQVWVTEVDPICALQAAMEGYRVV
TMDYAAEMADIFVTCTGNYHVITHDHMVKMKDQAIVCNIGHFDNEIDVAS
MKKYTWDNIKPQVDHIILPNGNRIILLAEGRLVNLGCGTGHPSYVMSSSF
ANQTIAQIELFTNTEAYPVGVYTLPKHLDEKVARLQLKKLNAVLTELSDE
QAAYIGVKKEGPYKPNHYRY conserved hypothetical protein [Oxalobacter
formigenes OXCC13] gi|237747886|ref|ZP_04578366.1|
SEQ ID NO: 13
MANQEEPIKVTDDFKQCWQSAGRHLQSQVEGGLTWMRASLDEPFMEHLSF
RLGNQLFFVRVIDVDNELKVPGTDENLIKIAEGCKGHACIMPMRFSFGNW
MPVEKGWGLLSAVDKKPVNPPDLVTDEKIEMTDWELHDFAVQVVRQNLMH
EGEHVAGWVSNPELQPSIWISTEEFPQWVVVQAVRWPAEAKIPDNIKEIE
DAYASKEAKGTFAYVTFANENQNVKEPLKEGEKPLPIYRGDKAYISYSGL
LSTEN diaminopimelate dehydrogenase [Oxalobacter
formigenes OXCC13] gi|237749390|ref|ZP_04579870.1|
SEQ ID NO: 14
MTTIKAAVHGLGNIGRHVIDCLTCAPDFECLGVIRRESSLGTQTLERRNI
PDYASIDKLIAEKGKPDVVI
LCGPSRSVPEDAKFYLSRGIRTVDSFDIHTDIAELVEKLDVVAKENNSAC
ITARTAGWDPGTDSVFLFEAMAPTGTTFTNFGRGRSMGHSVAARAIKGVA
DATSITIPIGGGRHARLVYVLAEKGASFEQIKKDLASDPYFSHDPLDVRE
VKTPEEMEAVADNSHGVLMERIGASGRTSNQNLTFTMKIDNPALTSQVLV
SCARAVTRMGAGCHTLIDVPPVMLLAGERMQHIARLV serine hydroxymethyltransferase [Oxalobacter
formigenes OXCC13] gi|237749274|ref|ZP_04579754.1|
SEQ ID NO: 15
MFAKDYSLAQVDSELWDAILRENTRQEEHIELIASENYCSPAVMQAQGSQ
LTNKYAEGYPGKRYYGGCEYVDIAEQLALDRVKKLFGAEAANVQPNSGSQ
ANQAIFLAMLNPGDTIMGMSLAEGGHLTHGMALNMSGKWFNVVSYGLNEK
EEIDYDRMEQLAHEHKPKLIIAGASAYSLRIDFERFAKVARDVGAFFMVD
MAHYAGLIAAGVYPSPVPYADFVTSTTHKSLRGPRGGFILMKPEFERKIN
SAVFPGLQGGPLMHVIAGKAVAFKEALQPEFKTYQEQVLKNASVLAKTLV
DRGFRIISGRTESHVMLVDLQSKNITGRQAETILNSGHITCNKNAIPNDP
QTPFVTSGVRLGSPAMTTRGFKETESAIVGNLLADVIENPNDQATIERVR
AEVKKLTTAFPVYQH aspartate-semialdehyde dehydrogenase [Oxalobacter
formigenes OXCC13] gi|237748872|ref|ZP_04579352.1|
SEQ ID NO: 16
MKLVGLIGWRGMVGSVLMQRMQEENDFDLFEPVFFTTSNVGGKAPAMAKN
ETVLKDAFNIDELKKCDILISCQGGDYTVDVFPKLRAAGWDGYWIDAASK
LRMNDDALIILDPVNRKVIEDGLSKGIKNYIGGNCTVSCMLMGLGGLFEN
DLVEWMTSMTYQAASGGGAQHMRELLTQFGSIHTEVRMNLENPASAILEI
DRQVLARQRGMTADETKQFGVPLAGNLIPWIDTLGNGMSREEWKGGAET -continued
NKILGKNDGNKVIVDGLCVRVGAMRCHSQALTIKLKKDVPLDEITDILKS

HNQWAKVVPNTKEDSVRDLTPAAVSGSLTIPVGRLRKLEMGNDYLSAFTV

GDQLLWGAAEPLRRMLRIILE

```
malic enzyme [Oxalobacter formigenes OXCC13]
gi|237749327|ref|ZP_04579807.1|
                                    SEQ ID NO: 17
```
MNSQDQKKELLKKNALAFHRFPIPGKISVNPTKEVRDQNELALAYTPGVA

CACEEIHANPENAYIYTTKGNLVAVISNGTAVLGLGNIGAQASKPVMEGK

GVLFKKFADINVFDLEINELDPDKLCDIIASLEPTFGGINLEDIRAPECF

YIERKLREKMNIPVFHDDQHGTAVIVGAAVLNALKVVGKNIKNCKMVVSG

VAGAGAMGCLELLDLGFPVENIWVTDIKGVVYKGRKELMDPEKEKYAQET

DARTLMDVISDADIFLGLSAGNVLKPEMVLKMAKDPVIFAMANPIPEILP

EVAHATRDDVIMGTGRSDYPNQINNSMCFPYLFRGALDCRAKTINREMEL

AAVRAIASLAEMECPEEIVAMYGKKYTFGRDYLLPFQFDPRLLWVVAPAV

AQAAMDSGVARVQIADMDAYRAKLKEFVG

```
aconitate hydratase 1 [Oxalobacter formigenes
OXCC13] gi|237747686|ref|ZP_04578166.1|
                                    SEQ ID NO: 18
```
MSCFTQNTYKEFPVTHEKKGHFYSIPALGKELGLDLSRLPVSIRIVLESV

LRNCDGKKITEEHVRQLANWKPNEERSNEIPFVVARVILQDFTGIPLLVD

LAAMRNVAVKTGKNPKKIEPLVPVDLVVDHSVQIDYFRQDNALDLNMKLE

FDRNRERYQFMKWGMQAFDTFGVVPPGFGIVHQVNMEYLARGVHKRNDAE

AGDVYYPDTLVGTDSHTTMINGVGVVGWGVGGIEAEAGMLGQPVYFLTPD

VIGMNLTGKLREGCTATDLVLTITELLRKEKVVGKFVEFFGEGAASLSAT

DRATIANMAPEYGATIGFFTVDEATISYFKNTGRTDEEVSALESYFRAQG

MFGIPKAGQIDYTRVVNLDLGSVTASVSGPRRPQDRIELGNLKKRFTELF

SAPVKDGGFNKKPADMEATYVNSDNVELKNGDILIAAITSCTNTSNPAVL

LAAGLLAKKAVEAGLQVSPRIKTSLAPGSRIVTNYLEKAGLLPYLEKLGF

NVAAYGCTTCIGNAGDLTPAMNEAIVKNDVVAAAVLSGNRNFEARIHPNI

RANFLASPPLVVAYAIAGNVTRDLTTEPLGKGKDGKDIYLSDIWPTSHEV

AALVPLALDAPSFRKNYSDIKTAPGELWQKIAGFATGDVYDWPQSTYIAE

PPFFSDFGMEPNAASANISGARALALFGDSITTDHISPAGSIQEKSPAGQ

WLMEHGISKANFNSFGSRRGNHEVMMRGTFGNVRIKNQMLPVGPDGSRRE

GGYTLYQPGGEETSIFDAAMRYQKENVPTIVIGGEEYGTGSSRDWAAKGT

QLLGVKAVIARSFERIHRSNLVGMAVLPLQFTGNDSAESLGLKGDETFDL

TGLDDITPLQDVTLVVHRADGTTQNVPLLLRIDTPIEVDYYRHGGILPFV

LRQLLSN

```
hsp70-like protein [Oxalobacter formigenes OXCC13]
gi|237749571|ref|ZP_04580051.1|
                                    SEQ ID NO: 19
```
MSKIIGIDLGTTNSCVAIIEGSQPRVVENSEGNRTTPSVIAYLDDGEILV

GAPAKRQAVTNPKNTLYAIK

RLIGRKFDDKEVQRDIPIMPFSIIKAENNDAWVSVLNDKKLAPPQVSAEV

LRKMKKTAEDYLGEEVTEAV

ITVPAYFNDAQRQATKDAGRIAGLDVKRIINEPTAAALAFGLDKAGKGDK

-continued
KIAVYDLGGGTFDISIIEIA

DLDGDKQFEVLSTNGDTFLGGEDFDQRIIDFIIDEFNKINGIDLKKDPIA

LQRIKASAERAKIELSSSQQ

TEINEPYIAMANGAPVHLNMKLTRAKLESLAEGLIDQTIEPCRIALKDAG

LSVSDIDDVILVGGMTRMPA

VQDKVKAFFGKEPRKDINPDEAVAVGAALQGAVLSGDRKDLLLLDVTPLS

LGIETLGGVMTKMIQKNTTIPTKFSQIFSTAEDNQPAVTIKVYQGEREMA

AGNKALGEFNLEGIPASPRGMPQIEVTFDIDANGILHVSAKDKATGKENK

ITIKANSGLSEDEIQRMIKDAEVNAAEDHKVRELTEARNQGDALVHTTKK

SMEEYGDKLDAPAKESIESAIKDLEESLKGDDKADIDSKMSALSAAAQKL

GEKMYADQAPEGAAAGAAGAGASAGAAPEPELEDDVVDADFKEVKDKD

Example 5

Description of Physico-Chemical Characteristics of Identified Secretagogues.

Methods

Calculation of Protein Extinction Coefficient of Native Protein in Water:

Protein extinction coefficient calculations used were as described by Edelhoch (Edelhoch, H., (1967) [PubMed: 6049437] using extinction coefficients for Tyr and Trp determined by Pace (Pace, C. N., et al., (1995) [PubMed: 8563639].

Calculation and Interpretation of Instability Index:

The instability index was determined as described by Guruprasad, K., et al., (1990) [PubMed: 2075190] and provides and estimate of the stability of the protein in a test tube. A stability index lower than 40 is predicted as stable while a value above 40 predicts that the protein may be unstable.

Calculation of Aliphatic Index:

Aliphatic index is defined as the relative volume occupied by aliphatic side chains (alanine, valine, isoleucine, and leucine) and is calculated according to the formula described by Ikai (Ikai, A. J. (1980) [PubMed: 7462208]. It may be regarded as a positive factor for the increase of thermostability of globular proteins.

Calculation of Grand Average of Hydropathy (GRAVY)

GRAVY is calculated as the sum of amino acid hydropathy values, divided by the number of residues in the sequence (Kyte, J., Doolittle, R. F. (1982) [PubMed: 7108955]. See Table 2 below.

Example 6

Identification of Putative Signal Peptide Cleavage Sites in the Amino Acid Sequence of the Identified Secretagogues.

Methods

Identification of putative presence and location of signal peptide cleavage sites was performed using the online prediction services provided by The Center for Biological Sequence Analysis at the Technical University of Denmark (http://www.cbs.dtu.dk/services/).

Prediction of Presence and Location of Twin-Arginine Signal Peptide Cleavage Sites in Bacteria:

The prediction of twin-arginine signal peptides was performed as described by Jannick Dyrløv Bendtsen et al (*BMC bioinformatics*, 6:167, 2005).

Results:

One protein of the nineteen proposed secretagogues had a sequence that was positive for a twin-arginine signal peptide cleavage site: YgiW protein (accession number: gi|237748090). The max. C, max. Y, max. S, mean S and max. D all gave a positive (YES) response for a signal peptide cleavage site with a value of 0.872, 0.500, 0.797, 0.314 and 0.407, respectively. The likely cleavage site is between position 28 and 29: ASA-QY.

Two additional proteins had a sequence that was positive for a signal peptide cleavage site in max. C but which was not confirmed in max. Y: phospho-2-dehydro-3-deoxyheptonate aldolase and cysteine synthase A.

Example 7.1

Recombinant Expression of the Identified Potential Secretagogue Compounds

Methods

The enzymes and proteins identified and outlined herein may be recombinantly expressed in the native host or a host of choice, suitable for recombinant overexpression as known by those skilled in the art. The recombinantly expressed enzymes and proteins will comprise a sequence having at least 85% sequence identity to the sequences outlined (SEQ No 1-19). Protein homologs and variants include but are not limited to: polymorphic variants and natural or artificial mutants, modified polypeptides in which one or more residue is modified, and mutants comprising one or more modified residues. Mutations include but are not limited to truncation, deletion, substitution or addition mutations of nucleic acids.

The recombinant enzymes may be expressed in a wide variety of hosts, known to those skilled in the art of protein expression, including but not limited to: *E. coli, Lactobacillus* spp, *Bacillus* spp etc.

For a recombinant production of the enzyme or protein the host should comprise a construct in the form of a plasmid, vector, phagemid, or transcription or expression cassette that comprises the enzyme or protein or a functional fragment thereof. A variety of constructs are available, including constructs, which are maintained in single copy or multiple copy. Many recombinant expression systems, components, and reagents for recombinant expression are commercially available, for example from Invitrogen Corporation (Carlsbad, Calif.); U.S. Biological (Swampscott, Mass.); BD Biosciences Pharmingen (San Diego, Calif.): Novagen (Madison, Wis.); Stratagene (La Jolla, Calif.); and Deutsche Sammlung von Mikroorganismen und Zellkulturen GmbH (DSMZ), (Braunschweigh, Germany).

A heterologous promotor, including a constitutive and/or inducible promotor, optionally controls recombinant expression of the proteins. Promotors such as, for example, T7 or other promotors, as suitable for the host, and which are well-known for those skilled in the art. The promotor may also originate from the *Oxalobacter* genus.

The enzyme or proteins recombinant nucleic acid sequence may include nucleic acids for purposes additional to the expression of the protein, including but not limited to for purification purposes, folding purposes etc. Examples of those are: secretion sequences, signal sequences, linkers, expression control elements, affinity tags, to name a few. The amino acids resulting from these nucleic acid sequences may or may not be removed after expression of the protein. All the constructs mentioned above may be used for expression of the enzymes and proteins, which will be used in methods described herein.

The host cells will be transformed/transfected with the chosen expression system, outlined above. The cells will be cultured using methods known to those skilled in the art, this include liquid cultures in shake flasks and fermenters as well as solid cultures in plates etc.

The proteins may be purified from the source, such as a natural or recombinant source, prior to being used in methods outlined herein. Purification may comprise extraction from the host cells by means of sonication, French press, glass beads or other mean of physical lysis, or chemical cell lysis, and separation by chromatographic steps or other means as known for those skilled in the art. Optionally, a concentration step may be used, e.g., by dialysis, chromatofocusing chromatography, and/or associated with buffer exchange.

Example 7.2

As outlined above in Example 7.1, of the enzymes and proteins identified and outlined herein, SEQ ID No:s 3, 4, 6, 13 and 19 were recombinantly overexpressed in *E. coli*, according to commonly used methods and techniques (Methods in Molecular Biology, Book 705, Thomas C. Evans Jr., Ming-Qun Xu, Humana Press; 2011; Methods in Molecular Biology, Book 235, Nicola Casali, Andrew Preston). The recombinantly expressed proteins originated from a synthesized gene sequence having at least 99% sequence identity to the sequences of SEQ ID No:s 3, 4, 6, 13 and 19 of Example 4. No mutations were performed to the sequences presented in Example 4 but short sequence tags were added to facilitate purification (Histidine tag). Purified protein molecular weight and identity were confirmed by way of SDS-PAGE and Western blot. SDS-PAGE was run on 4%-20% gradient gel, followed by Coomassie Blue staining. The Western blot analysis utilized Anti-His Antibody from Genscript, Cat. No. A00612 or A00186.

Results

The proteins were successfully overexpressed and purified from *E. coli* culture supernatant by use of Histidine tag affinity purification, to near homogeneity (approximately 85% purity). The final storage buffer for all proteins was 50 mM Tris-HCl, 150 mM NaCl, 10% Glycerol, pH 8. Theoretical molecular weight was confirmed with SDS-PAGE gel for all proteins except SEQ ID No. 3 and SEQ ID No. 4, for which migration on the gel insinuated a larger molecular weight than expected. However, for both proteins the theoretical molecular weight was confirmed by Maldi-TOF. Further, such anomalous behaviour on SDS-PAGE gel is consistent with observations from in particular acyl carrier proteins of other bacteria (*J. Bacteriol.* 178:4794-4800, *J. Biol. Chem.* 267:5751-5754, *J. Bacteriol.* 174:3818-3821) and has been attributed to the high charge-to-mass ratio as well as its low hydrophobic amino acid content, two factors that have a considerable influence on SDS binding (J. Biol. Chem. 254:9778-9785), and thus can be the cause of this anomaly for both SEQ ID No. 3 and SEQ ID No. 4.

Purity of all proteins was determined by densitometric analysis of Coomassie Blue-stained SDS-PAGE gel to approximately 85% (FIG. 1 A-E). Bovine Serum Albumin (2 ug) was run as control (Lane 1). Target protein on SDS-PAGE gel is presented in Lane 2, and target protein on Western blot is presented in Lane 3.

FIG. 1A: SEQ ID No. 3 expressed protein analysis. Anti-His antibody used: Genscript Cat. No. A00612.

FIG. 1B: SEQ ID No. 4 expressed protein analysis. Anti-His antibody used: Genscript Cat. No. A00612.

FIG. 1C: SEQ ID No. 6 expressed protein analysis.

Anti-His antibody used: Genscript Cat. No. A00612.
FIG. 1D: SEQ ID No. 13 expressed protein analysis.
Anti-His antibody used: Genscript Cat. No. A00186.
FIG. 1E: SEQ ID No. 19 expressed protein analysis.
Anti-His antibody used: Genscript Cat. No. A00186.

Example 8

Screen of Potential Secretagogues Using Intestinal Cell Model
Methods

Using human intestinal Caco2-BBE cells, T84 or another cell line suitable for simulating transport over intestinal epithelia, the effect of *Oxalobacter formigenes* conditioned medium and/or recombinantly expressed secretagogues may be screened for altered net oxalate transport over the cell layer. In the case of evaluation of conditioned media the cells will be pre-incubated with a suitable dilution (e.g. 1:50) of *O. formigenes* conditioned media and unconditioned media, as well as *Lactobacillus Acidophilus* conditioned media, for 24 h. The apical [$^{14}$C] oxalate influx will be measured in the presence of an outward Cl gradient. In the case of evaluation of recombinantly expressed proteins the cells will be pre-incubated with either a suitable concentration of purified protein or a cell lysate from the expression host. Several dilutions will be included to evaluate dose-response. As controls the protein buffer or the untransformed host cell lysate will be used, respectively.

Example 9.1

Screen of Potential Secretagogues Using Intestinal Tissue from Animal
Methods

As a method to screen potential secretagogue compounds intestinal tissue can be isolated from mice or rats. The animals are euthanized using 100% $CO_2$ and the intestine is immediately removed. The tissue is thoroughly cleansed using ice-cold 0.9% NaCl, connective tissue is removed, and the segments are opened along the mesenteric border. Flat sheets of tissue are mounted in a modified Ussing chamber and tissue is bathed on both sides by buffered saline (pH 7.4) containing 1.25 uM oxalate at 37° C., while bubbling with 95% $O_2$, 5% $CO_2$. The two unidirectional fluxes of [$^{14}$C] oxalate will be measured at suitable time intervals under short-circuit conditions using an automatic voltage clamp. The electrical parameters of the tissue will be measured (open-circuit potential, short-circuit current etc.) throughout the experiment. Details to planned experiments are described in the art (Hatch and Freel Am J Nephrol 23: 18-26, 2003, Freel et al *Am J Physiol Gastrointest Liver Physiol* 290: G719-G728, 2006).

The animals that may be suitable to use include but are not limited to Sprague-Dawley rats with or without hyperoxaluria induction using ethylene glycol, AGT knock-out mice (C57BL/6 background strain as described by Salido et al (*PNAS USA* 103: 18249-18254, 2006), or transport protein knock-out mice e.g. Slc26a6$^{-/-}$ (Wang et al., *Am J Physiol Cell Physiol* 288: C957-C965, 2005).

The intestinal tissues used for transport studies will be derived from the above described strains of mice or rats, raised using an oxalate containing diet or not. The animals may also be repeatedly gavaged with live cultures of *O. formigenes* to induce colonization, while fed an oxalate containing diet or not.

To confirm colonization and state of hyperoxaluria, urine and fecal samples will be collected during the housing of the animals and analyzed for oxalate and *O. formigenes* as thoroughly described in the art. Animals will be confirmed non-colonized before any attempts to colonize using *O. formigenes*.

To confirm potential secretagogue action on an anion exchange transport protein, suitable inhibitors may be added to the Ussing chamber compartments, these include but are not limited to DIDS (4,4'-diisothiocyano-2,2'-stilbene disulfonate), and SITS (4-acetamido-4'-isothiocyanostilbene 2'-disulfonate).

Example 9.2

Screen of Recombinantly Expressed Potential Protein Secretagogues from *Oxalobacter formigenes* Using Intestinal Tissue from Rat
Methods
Ussing Chamber Experiment As outlined above in Example 9.1, intestinal segments were stripped of muscle layers and mounted in Ussing chambers, each side bathed in 5 ml of glucose-Ringer solution containing 1.5 μM (unlabelled) sodium oxalate (Ringer composition in mmol/L: Na$^+$ 140, Cl$^-$ 119.8, K$^+$ 5.2, HCO$_3^-$ 25, Ca$^{2+}$ 1.2, Mg$^{++}$ 1.2, HPO$_4^{2-}$ 2.4, H$_2$PO$_4^-$ 0.4, glucose 10, pH 7.4 when gassed with 95% $O_2$/5% $CO_2$ at 37° C.). Direct recording of trans mural electrical potential difference (PD) in mV and determination of short-circuit current ($I_{SC}$) in μA/cm$^2$ was performed using two sets of electrodes connecting the chamber solutions to voltage clamps. Total electrical resistance ($R_T$) in ohms·cm$^2$ was calculated using Ohm's Law, where PD=$I_{SC} \times R_T$.

All experiments were conducted under short circuit conditions except when periodically switched to the open circuit state for recording of PD. At T=0 min, treatments were added to the mucosal solution of the pair. Tissues were short-circuited and equilibrated for 20 min while reading $I_{SC}$ and $R_T$. At T=20 min 10 μCi of labeled C14-oxalate was added to either the mucosal or serosal bath, of one of the paired tissues. At T=30 min flux sampling of 100 μl every 15 min, from the unlabelled side, was started, and continued for a 60 min period. The 100 μl of solution from the 'unlabelled' side was replaced with 100 μl of unlabelled buffer. Aliquots (100 μl) of the 'hot' side solution were taken at the beginning and end of experimental periods and their values averaged to obtain the specific activity for the period. Isotope activity was measured with a liquid scintillation counter. Unidirectional fluxes were computed ($J^{ox}$=cpm/time·specific activity·area) and expressed as umol/min·cm$^2$. Net fluxes were calculated as the difference in the unidirectional fluxes between paired specimens. $I_{SC}$ in μA (converted to μEq/cm$^2$·hr) and PD in mV were recorded at the start and end of each sampling interval and averaged for that interval.

The control (only buffer) was evaluated identically to the test article, using Sprague-Dawley rat distal colon tissue. The test articles entailed the recombinantly expressed proteins of Example 7.2 divided into three groups: Group 1: Protein of SEQ ID No. 3, Group 2: Proteins of SEQ ID No. 4 and 19, Group 3: Proteins of SEQ ID No. 6 and 13. Tissues from six rats were used per treatment (n=6). Differences between basal mucosal-to-serosal (m-s) and serosal-to-mucosal (s-m) fluxes of C14-oxalate for paired tissues is used to establish net absorption (m-s>s-m) or secretion (s-m>m-s) of oxalate for a specific treatment. Calculation of the mean+/−SEM of the net flux for all treatments determines if there is an effect from a treatment over the respective control.

Results

The buffer control demonstrated net absorptive flux for this distal intestinal segment of rat tissue, confirming prior literature studies with similar intestinal rat segments. The flux was measured in two periods, 0-30 minutes and 30-60 minutes. Similar behaviour of the control was seen in both periods. In both periods, the treatments of the three groups all reduce the total flux of labeled oxalate. However, in the later period Group 1 demonstrate a larger change in serosal-to-mucosal (s-m) flux, resulting in a larger net secretion over the intestinal tissue, of labeled oxalate, in this period. Due to one outlier replicate, only five replicates of the experiment were included in this data set.

Figure 2:
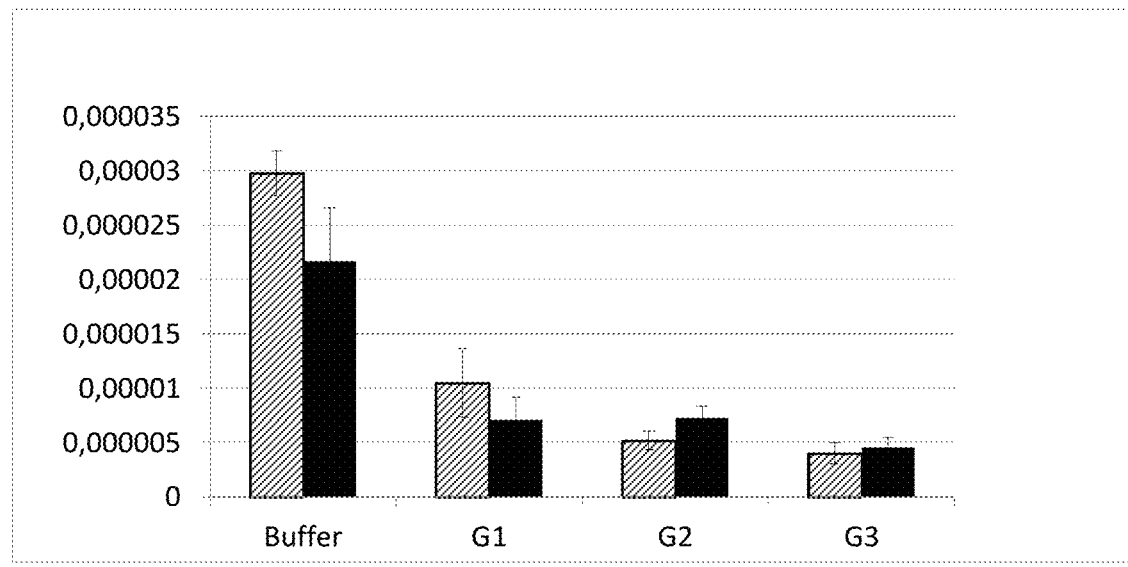
FIG. 2. Bar chart showing flux of labeled oxalate (C14-oxalate) during first flux period, 0-30 minutes. Striped bars depict mucosal-to-serosal flux (M-S flux), and filled bars depict serosal-to-mucosal flux (S-M flux). On the horizontal axis, G1-G3 denote the three groups of treatment, G=group. Error bars=±SEM (standard error of mean). The vertical axis shows 14C-oxalate in umol·cm2·h.

FIG. 2 depicts labeled oxalate flux during first flux period, 0-30 minutes (T=30 to T=60, as per "Ussing Chamber Experiment" denotations). M-S flux=mucosal-to-serosal flux, S-M flux=serosal-to-mucosal flux. G1-G3 denote the three groups of treatment, G=group.

Figure 3:
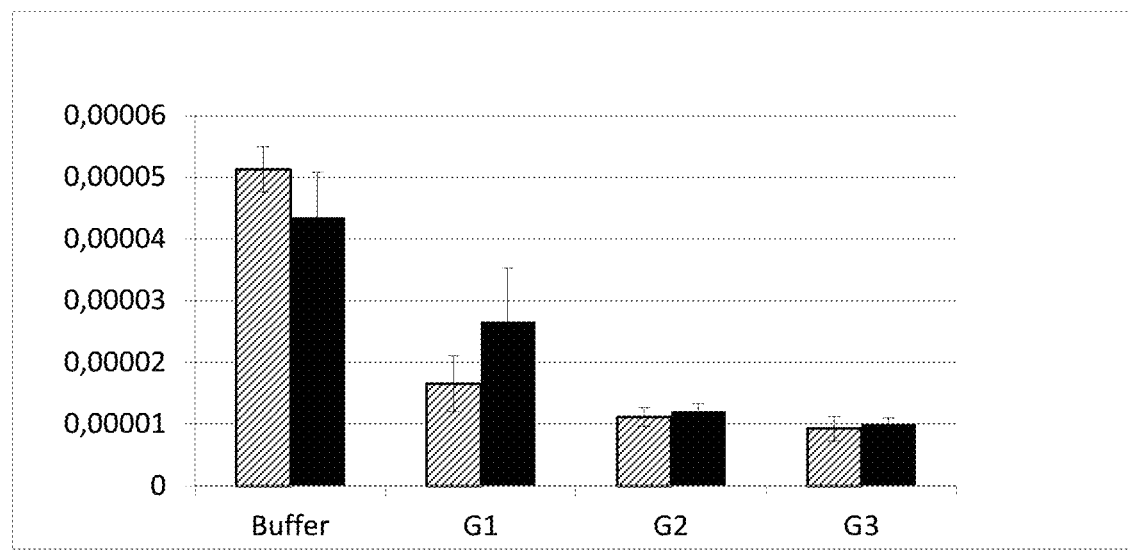
FIG. 3. Bar chart showing flux of labeled oxalate (C14-oxalate) during second flux period, 30-60 minutes. Striped bars depict mucosal-to-serosal flux (M-S flux), and filled bars depict serosal-to-mucosal flux (S-M flux). On the horizontal axis, G1-G3 denote the three groups of treatment, G=group. Error bars=±SEM (standard error of mean). The vertical axis shows 14C-oxalate in umol·cm2·h.

FIG. 3 shows labeled oxalate flux during second flux period, 30-60 minutes (T=60 to T=90, as per "Ussing Chamber Experiment" denotations). M-S flux=mucosal-to-serosal flux, S-M flux=serosal-to-mucosal flux. G1-G3 denote the three groups of treatment, G=group.

Example 10

Evaluation of Expression Pattern of Transport Proteins In Vivo

To confirm presence of transport proteins in vivo, in particular proteins belonging to the class of SLC26A (solute-linked carrier), mucosal scrapings can be analyzed using suitable immunoblotting and probing, methods which are well described in the art and described herein in brief.
Methods The mucosal scraping would be analyzed using SDS-PAGE and subsequently transferred onto a nitrocellulose membrane. The membrane would be blocked with for example a 1% casein solution, washed with phosphate buffered saline containing detergent and then probed using a specific primary antibody and subsequently a suitable secondary antibody linked to a enzyme for detection e.g. HRP (horse radish peroxidase) enzyme.

The primary antibodies may be raised against recombinantly expressed transport proteins and used to detect for specific transport proteins e.g. SLC26a6. Methods for preparation of antibodies is common place in the art and will not be outlined herein.

Example 11

Evaluation of Binding Interactions Between Recombinantly Expressed Transport Proteins and Potential Secretagogue Compounds As a complementary or alternative way to screen the identified potential secretagogue compounds for the compound/s with the desired characteristics the interaction between the transporter/s and the proposed secretagogue compounds can be analyzed.
Methods There are several suitable methods to characterize protein-protein interactions, known to those skilled in the art. For example various indirect methods i.e. ELISA, RIA and surface plasmon resonance may be used to characterize the interaction between the oxalate transporter membrane protein and the expressed and purified potential secretagogue. Also, Isothermal Titration calorimetry (ITC) can be used to quantify the interactions by determining the heat evolved on protein-protein association.

Example 12

Evaluation of Potential Secretagogues in Hyperoxaluria Animal Models

Following a screen of the recombinantly expressed potential secretagogues in vitro, the promising compounds will be included in a study using suitable animal models (see Example 9 for examples of animal models that may be used as described herein), to confirm the effect in vivo. This study may be performed using a respective arm for the concurrent colonization with *O. formigenes*, or the lack of colonization.
Methods Several animal models have been used to simulate hyperoxaluric conditions, among one is the AGT knock-out mouse model (see Example 9). This mouse model may be used to evaluate the potential secretagogue compound. The execution for these animal models is well described in the literature and will only generally be described herein. Further, methods for plasma and urinary oxalate and calcium analysis are commonly used in the field and will not be outlined.

Both female and male mice will be used. In the beginning of the study (approx. 5 days) the mice will be given free access to water and standard mouse chow (e.g. diet 2018S, Harlan teklad) to establish a base line value for the parameters to be monitored, including but not limited to plasma and urinary oxalate and calcium.

In order to increase contrast in oxalate levels and/or facilitate *O. formigenes* colonization a period (approx. 5 days) in which the mice are primed with a high oxalate diet may be incorporated (e.g. 1.5% oxalate supplemented diet (0.5% calcium; diet 89000, Harlan Teklad). If desired, a select arm will be colonized with *O. formigenes* by esophageal gavage of a 0.5-mL inoculum containing wet *O. formigenes* cell pellet at two occasions, with 48 hours separation. The control group will be gavaged with an inactivated *O. formigenes* culture or similar. After five days the colonization is confirmed in the respective animals using detection in fecal samples by PCR and the administration of the secretagogue compound can ensue for both groups.

Each group may be divided into separate arms in which the secretagogue is administrated or not, secretagogue administration may continue for 3-5 days. Throughout the study plasma and urinary oxalate and calcium will be monitored. Subsequently of ending administration of product a period of continued high-oxalate diet may be performed in order to see the parameter values return to pre-secretagogue levels. If desired, a separate arm of the colonized animals given product may be kept on product but returned to regular oxalate level diets (0.5%) in order to evaluate if the knock-out mice can sustain colonization without exogenous addition of oxalate.

TABLE 1

Identified proposed secretagogues

| SEQ ID No | Identified Proteins | Accession Number | Molecular Weight |
|---|---|---|---|
| 1 | Tartronic semialdehyde reductase [Oxalobacter formigenes OXCC13] | gi|237749254 | 30 kDa |
| 2 | Cysteine synthase A [Oxalobacter formigenes OXCC13] | gi|237748046 | 32 kDa |
| 3 | Acyl carrier protein [Oxalobacter formigenes OXCC13] | gi|237747699 | 9 kDa |
| 4 | Predicted protein [Oxalobacter formigenes OXCC13] | gi|237749499 | 10 kDa |
| 5 | Methionine adenosyltransferase 1 [Oxalobacter formigenes OXCC13] | gi|237747590 | 42 kDa |
| 6 | YgiW protein [Oxalobacter formigenes OXCC13] | gi|237748090 | 14 kDa |
| 7 | Riboflavin synthase subunit beta [Oxalobacter formigenes OXCC13] | gi|237749243 | 18 kDa |
| 8 | Alkyl hydroperoxide reductase/Thiol specific antioxidant/Mal allergen [Oxalobacter formigenes OXCC13] | gi|237747586 | 21 kDa |
| 9 | Chain A, Formyl-Coa Transferase With Aspartyl-Coa Thioester Intermediate Derived From Oxalyl-Coa | gi|163931105 (+8) | 47 kDa |
| 10 | Phospho-2-dehydro-3-deoxyheptonate aldolase [Oxalobacter formigenes OXCC13] | gi|237749194 | 39 kDa |
| 11 | Elongation factor Tu [Oxalobacter formigenes OXCC13] | gi|237747517 | 39 kDa |
| 12 | S-adenosylhomocysteine hydrolase [Oxalobacter formigenes OXCC13] | gi|237749247 | 52 kDa |
| 13 | Conserved hypothetical protein [Oxalobacter formigenes OXCC13] | gi|237747886 | 29 kDa |
| 14 | Diaminopimelate dehydrogenase [Oxalobacter formigenes OXCC13] | gi|237749390 | 33 kDa |
| 15 | Serine hydroxymethyltransferase [Oxalobacter formigenes OXCC13] | gi|237749274 | 46 kDa |
| 16 | Aspartate-semialdehyde dehydrogenase [Oxalobacter formigenes OXCC13] | gi|237748872 | 41 kDa |
| 17 | Malic enzyme [Oxalobacter formigenes OXCC13] | gi|237749327 | 47 kDa |
| 18 | Aconitate hydratase 1 [Oxalobacter formigenes OXCC13] | gi|237747686 | 99 kDa |
| 19 | Hsp70-like protein [Oxalobacter formigenes OXCC13] | gi|237749571 | 70 kDa |

TABLE 2

Description of physico-chemical characteristics of identified secretagogues

| SEQ ID No | Identified Proteins | Theoretical pI | Extinction Coefficient* (M−1 cm−1) | Instability Index (II) | Aliphatic Index | GRAVY (Grand Average of Hydropathy) |
|---|---|---|---|---|---|---|
| 1 | Tartronic semialdehyde reductase [Oxalobacter formigenes OXCC13] | 6.44 | 1490** | 26.6 | 97.36 | 0.192 |
| 2 | Cysteine synthase A [Oxalobacter formigenes OXCC13] | 5.67 | 18450 | 24.48 | 97.39 | 0.094 |
| 3 | Acyl carrier protein [Oxalobacter formigenes OXCC13] | 3.79 | 1490** | 50.07 | 98.73 | −0.247 |
| 4 | Predicted protein [Oxalobacter formigenes OXCC13] | 4.91 | 1490** | 18.19 | 111.46 | −0.096 |
| 5 | Methionine adenosyltransferase 1 [Oxalobacter formigenes OXCC13] | 5.28 | 40340 | 38.67 | 89.28 | −0.261 |
| 6 | YgiW protein [Oxalobacter formigenes OXCC13] | 9.33 | 9970 | 12.05 | 91.19 | −0.147 |
| 7 | Riboflavin synthase subunit beta [Oxalobacter formigenes OXCC13] | 4.13 | 2980** | 53.34 | 103.64 | 0.073 |
| 8 | Alkyl hydroperoxide reductase/Thiol specific antioxidant/Mal allergen [Oxalobacter formigenes OXCC13] | 5.58 | 23950 | 30.91 | 89.68 | −0.069 |
| 9 | Chain A, Formyl-Coa Transferase With Aspartyl-Coa Thioester Intermediate Derived From Oxalyl-Coa | 5.26 | 57410 | 26.76 | 77.94 | −0.304 |
| 10 | Phospho-2-dehydro-3-deoxyheptonate aldolase [Oxalobacter formigenes OXCC13] | 5.98 | 29910 | 35.29 | 89.83 | −0.336 |
| 11 | Elongation factor Tu [Oxalobacter formigenes OXCC13] | 4.93 | 14900** | 30.39 | 92.11 | −0.15 |
| 12 | S-adenosylhomocysteine hydrolase [Oxalobacter formigenes OXCC13] | 5.63 | 68300 | 30.52 | 86.36 | −0.22 |
| 13 | Conserved hypothetical protein [Oxalobacter formigenes OXCC13] | 4.85 | 56950 | 39.86 | 77.96 | −0.444 |
| 14 | Diaminopimelate dehydrogenase [Oxalobacter formigenes OXCC13] | 6.31 | 11460 | 34.57 | 89.61 | −0.058 |
| 15 | Serine hydroxymethyltransferase [Oxalobacter formigenes OXCC13] | 6.28 | 33350 | 41.01 | 82.8 | −0.233 |
| 16 | Aspartate-semialdehyde dehydrogenase [Oxalobacter formigenes OXCC13] | 5.45 | 51450 | 30.85 | 93.56 | −0.141 |
| 17 | Malic enzyme [Oxalobacter formigenes OXCC13] | 5.32 | 28880 | 30.75 | 95.52 | −0.007 |
| 18 | Aconitate hydratase 1 [Oxalobacter formigenes OXCC13] | 5.69 | 84230 | 32.64 | 88.06 | −0.156 |
| 19 | Hsp70-like protein [Oxalobacter formigenes OXCC13] | 4.76 | 18910 | 34.69 | 91.03 | −0.322 |

The invention claimed is:

1. A pharmaceutical composition comprising an effective amount of a secretagogue isolated from *Oxalobacter formigenes* oxalate-degrading bacteria, the secretagogue having the amino acid sequence of any one of SEQ ID NOs. 3, 4, 6, 13 and 19, wherein the secretagogue promotes secretion of oxalate, and wherein the pharmaceutical composition is provided with an enteric coating.

2. The pharmaceutical composition according to claim 1, further comprising oxalate-degrading *Oxalobacter formigenes* bacteria.

3. The pharmaceutical composition according to claim 1, further comprising one or more selected from oxalate-degrading enzymes, enzymes involved in oxalate metabolism, cofactors selected from vitamin $B_6$, $NAD^+$, $NADP^+$, FAD, CoA, ATP and ADP, substrates selected from oxalate, glyoxylate, and 4-hydroxy-2-oxoglutarate, and combinations of any thereof.

4. The pharmaceutical composition according to claim 1, wherein the secretagogue is selected from recombinantly expressed secretagogues and secretagogues extracted from conditioned media.

5. The pharmaceutical composition of claim 1, wherein the pharmaceutical composition is in the form of a tablet, capsule, or bead provided with the enteric coating.

6. The pharmaceutical composition of claim 1, wherein the secretagogue has the amino acid sequence of SEQ ID NO: 3.

7. The pharmaceutical composition of claim 1, wherein the secretagogue has the amino acid sequence of SEQ ID NO: 4.

8. The pharmaceutical composition of claim 1, wherein the secretagogue has the amino acid sequence of SEQ ID NO: 6.

9. The pharmaceutical composition of claim 1, wherein the secretagogue has the amino acid sequence of SEQ ID NO: 13.

10. The pharmaceutical composition of claim 1, wherein the secretagogue has the amino acid sequence of SEQ ID NO: 19.

11. A method for reducing oxalate in a subject in need thereof, comprising administering to said subject (i) an effective amount of the composition of claim 1, and (ii) oxalate-degrading *Oxalobacter formigenes* bacteria, wherein the secretagogue and the oxalate-degrading *Oxalobacter formigenes* bacteria are administered from separate compositions, and wherein the method is effective to reduce urinary and/or plasma oxalate in the subject.

12. A method for reducing oxalate in a subject in need thereof, comprising administering to said subject an effective amount of the composition of claim 2, wherein the method is effective to reduce urinary and/or plasma oxalate in the subject.

13. A method for reducing oxalate in a subject in need thereof, comprising administering to said subject an effective amount of the composition of claim 1, wherein the method is effective to reduce urinary and/or plasma oxalate in the subject.

14. The method according to claim 13, further comprising administering to said subject one or more selected from oxalate-degrading enzymes, enzymes involved in oxalate metabolism, cofactors selected from vitamin $B_6$, $NAD^+$, $NADP^+$, FAD, CoA, ATP and ADP, substrates selected from oxalate, glyoxylate, and 4-hydroxy-2-oxoglutarate, and combinations of any thereof.

15. The method according to claim 13, wherein the subject is suffering from an oxalate related disease and/or an oxalate related imbalance.

16. The method according to claim 15, wherein the oxalate related disease is selected from primary hyperoxaluria, hyperoxaluria, absorptive hyperoxaluria, enteric hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and disorders and conditions caused by or associated with gastrointestinal surgery, bariatric surgery, and/or antibiotic treatment.

17. A pharmaceutical product comprising:
(i) an effective amount of a secretagogue isolated from *Oxalobacter formigenes* oxalate-degrading bacteria, the secretagogue having the amino acid sequence of any one of SEQ ID NOs. 3, 4, 6, 13 and 19, wherein the secretagogue promotes secretion of oxalate, and
(ii) oxalate-degrading *Oxalobacter formigenes* bacteria, wherein the secretagogue and bacteria are in separate pharmaceutical compositions, each provided with an enteric coating.

* * * * *